(12) United States Patent
Yoshida

(10) Patent No.: US 10,275,677 B2
(45) Date of Patent: Apr. 30, 2019

(54) IMAGE PROCESSING APPARATUS, IMAGE PROCESSING METHOD AND PROGRAM

(71) Applicant: NEC SOLUTION INNOVATORS, LTD., Koto-ku, Tokyo (JP)

(72) Inventor: Amane Yoshida, Tokyo (JP)

(73) Assignee: NEC SOLUTION INNOVATORS, LTD., Tokyo (JP)

( * ) Notice: Subject to any disclaimer, the term of this patent is extended or adjusted under 35 U.S.C. 154(b) by 15 days.

(21) Appl. No.: 15/535,794

(22) PCT Filed: Dec. 25, 2015

(86) PCT No.: PCT/JP2015/086253
§ 371 (c)(1),
(2) Date: Jun. 14, 2017

(87) PCT Pub. No.: WO2016/104712
PCT Pub. Date: Jun. 30, 2016

(65) Prior Publication Data
US 2017/0344846 A1  Nov. 30, 2017

(30) Foreign Application Priority Data
Dec. 26, 2014 (JP) ................................ 2014-265768

(51) Int. Cl.
*G06K 9/00* (2006.01)
*G06K 9/40* (2006.01)
(Continued)

(52) U.S. Cl.
CPC ............. *G06K 9/40* (2013.01); *A61B 5/117* (2013.01); *A61B 5/1172* (2013.01);
(Continued)

(58) Field of Classification Search
CPC ...... G06K 9/40; G06K 9/0008; G06K 9/4642; G06K 9/6215; A61B 5/117; A61B 5/1172; A61B 5/7203; G06F 19/00
See application file for complete search history.

(56) References Cited

U.S. PATENT DOCUMENTS 7,835,568 B2 * 11/2010 Park ...................... G06T 17/10
382/154
8,180,121 B2 * 5/2012 Bolle .................. G06K 9/00073
283/68
(Continued)

FOREIGN PATENT DOCUMENTS

| JP | 2004-127064 A | 4/2004 |
| JP | 2007-048000 A | 2/2007 |

(Continued)

OTHER PUBLICATIONS

Koichi Ito et al., "A Study on Biometric Authentication Using Local Feature Descriptors", 29th Symposium on Cryptography and Information Security, Jan. 30, 2012, pp. 1-7.
(Continued)

*Primary Examiner* — Gregory M Desire

(57) ABSTRACT

An image processing device comprises an input unit, a characteristic amount calculation unit, a characteristic amount vector calculation unit, and a characteristic identification unit. The input unit receives an image. The characteristic amount calculation unit calculates an image characteristic amount characterizing a texture of a local area of the image received by the input unit. The characteristic amount vector calculation unit calculates a first characteristic amount vector corresponding to the local area from the image characteristic amount. The characteristic identification unit identifies a characteristic of the local area on the basis of the first characteristic amount vector and a second characteristic amount vector calculated by the same method
(Continued)

as the first characteristic amount vector and calculated from an image whose characteristic has been determined in advance.

13 Claims, 21 Drawing Sheets

(51) Int. Cl.
    *A61B 5/117*     (2016.01)
    *A61B 5/1172*     (2016.01)
    *A61B 5/00*     (2006.01)
    *G06K 9/46*     (2006.01)
    *G06K 9/62*     (2006.01)
    *G06F 19/00*     (2018.01)

(52) U.S. Cl.
    CPC ............ *A61B 5/7203* (2013.01); *G06F 19/00* (2013.01); *G06K 9/0008* (2013.01); *G06K 9/4642* (2013.01); *G06K 9/6215* (2013.01)

(56) References Cited

U.S. PATENT DOCUMENTS

| | | | |
|---|---|---|---|
| 8,965,066 B1* | 2/2015 | Derakhshani | H04L 9/14 |
| | | | 382/117 |
| 2002/0146178 A1 | 10/2002 | Bolle et al. | |
| 2004/0066850 A1 | 4/2004 | Nakajima et al. | |
| 2005/0063582 A1* | 3/2005 | Park | G06T 17/10 |
| | | | 382/154 |
| 2007/0036401 A1 | 2/2007 | Hara | |
| 2007/0160266 A1 | 7/2007 | Jones et al. | |
| 2007/0189586 A1 | 8/2007 | Monden | |
| 2008/0013803 A1 | 1/2008 | Lo et al. | |
| 2011/0091113 A1 | 4/2011 | Ito et al. | |
| 2011/0206246 A1* | 8/2011 | Wolf | G06F 19/24 |
| | | | 382/118 |
| 2015/0169942 A1* | 6/2015 | Hu | G06K 9/00288 |
| | | | 382/118 |
| 2017/0344846 A1* | 11/2017 | Yoshida | A61B 5/117 |

FOREIGN PATENT DOCUMENTS

| | | |
|---|---|---|
| JP | 2009-523265 A | 6/2009 |
| JP | 2011-086265 A | 4/2011 |
| JP | 2014-067174 A | 4/2014 |
| WO | 2005/086091 A1 | 9/2005 |

OTHER PUBLICATIONS

International Search Report for PCT Application No. PCT/JP2015/086253, dated Mar. 15, 2016.

* cited by examiner

FIG. 4

| CHARACTERISTIC OF LOCAL AREA | CHARACTERISTIC NAME |
|---|---|
| NO FINGERPRINT | NON-FINGERPRINT |
| FINGERPRINT WITHOUT NOISE | FINGERPRINT |
| SWEAT GLAND PORES ON RIDGES | SWEAT GLAND PORES |
| FADED RIDGES | FADED |
| ... | ... |

FIG. 7

| 213(1) | 214(1) | 215(1) |
|---|---|---|
| 212(0) | 210 | 216(0) |
| 211(0) | 218(1) | 217(0) |

FIG. 8

| CLASS (LBP) | FREQUENCY |
|---|---|
| LBP<32 | a1 |
| 32≦LBP<64 | a2 |
| 192≦LBP<224 | a7 |
| 224≦LBP | a8 |

FIG. 9

| LOCAL AREA (X, Y) | CHARACTERISTIC AMOUNT VECTOR (X, Y) |
|---|---|
| LA(0,0) | FV(0,0)={A1, A2, ···, A8} |
| LA(1,0) | FV(1,0)={B1, B2, ···, B8} |
| ... | ... |
| LA(10,5) | FV(10,5)={C1, C2, ···, C8} |
| ... | ... |
| LA(15,15) | FV(15,15)={D1, D2, ···, D8} |

FIG. 10

| IMAGE CHARACTERISTIC DATABASE | |
|---|---|
| CHARACTERISTIC NAME | CHARACTERISTIC AMOUNT VECTOR FV |
| NON-FINGERPRINT | FV1-1=[K1_1, K1_2, ..., K1_8] |
| | FV1-2=[K2_1, K2_2, ..., K2_8] |
| | ... |
| FINGERPRINT | FV2-1=[L1_1, L1_2, ..., L1_8] |
| | FV2-2=[L2_1, L2_2, ..., L2_8] |
| | ... |
| SWEAT GLAND PORES | FV3-1=[M1_1, M1_2, ..., M1_8] |
| | FV3-2=[M2_1, M2_2, ..., M2_8] |
| | ... |
| FADED | FV4-1=[N1_1, N1_2, ..., N1_8] |
| | FV4-2=[N2_1, N2_2, ..., N2_8] |
| | ... |
| ... | ... |

FIG. 11

| LOCAL AREA (X, Y) | CHARACTERISTIC OF LOCAL AREA |
|---|---|
| LA(0,0) | NON-FINGERPRINT |
| LA(1,0) | NON-FINGERPRINT |
| ... | ... |
| LA(10,5) | SWEAT GLAND PORES |
| ... | ... |
| LA(15,15) | NON-FINGERPRINT |

LOCAL AREA CHARACTERISTIC INFORMATION

FIG. 19

| IMAGE CHARACTERISTIC DATABASE | |
|---|---|
| CHARACTERISTIC NAME | CHARACTERISTIC AMOUNT VECTOR FV |
| NON-FINGERPRINT | FV1-1={K1_1, K1_2, ···, K1_8} |
| | FV1-2={K2_1, K2_2, ···, K2_8} |
| | ··· |
| FINGERPRINT | FV2-1={L1_1, L1_2, ···, L1_8} |
| | FV2-2={L2_1, L2_2, ···, L2_8} |
| | ··· |
| SWEAT GLAND PORES | FV3-1={M1_1, M1_2, ···, M1_8} |
| | FV3-2={M2_1, M2_2, ···, M2_8} |
| | ··· |
| FADED | FV4-1={N1_1, N1_2, ···, N1_8} |
| | FV4-2={N2_1, N2_2, ···, N2_8} |
| | ··· |
| SWEAT GLAND PORES + FADED | FV5-1={O1_1, O1_2, ···, O1_8} |
| | FV5-2={O2_1, O2_2, ···, O2_8} |
| | ··· |
| ··· | ··· |

IMAGE PROCESSING APPARATUS, IMAGE PROCESSING METHOD AND PROGRAM

REFERENCE TO RELATED APPLICATION

This application is a National Stage Entry of PCT/JP2015/086253 filed on Dec. 25, 2015, which claims priority from Japanese Patent Application 2014-265768 filed on Dec. 26, 2014, the contents of all of which are incorporated herein by reference, in their entirety.

TECHNICAL FIELD

The present invention relates to an image processing apparatus, image processing method and program, and particularly to an image processing apparatus, image processing method and program that identify a characteristics of an input image.

BACKGROUND

For a long time, fingerprint and palm print constituted by numerous ridges of curved stripes have been utilized as person identification means. Particularly, collation using a latent fingerprint left in a crime scene is used as effective investigation means. Many police agencies have implemented fingerprint matching systems using computers. By comparing the characteristics of fingerprint images registered in a database with those of a fingerprint left and taken in a crime scene, a person corresponding to the fingerprint can be identified. Further, endpoints and bifurcation points of fingerprint ridges are often used as the characteristics used in fingerprint matching.

Patent Literature 1 states that it provides a configuration capable of accurately extracting and removing pileous glands and sweat gland pores by extracting the characteristics of pileous glands, analyzing the appearance patterns thereof, and judging the pileous glands by means of a predetermined conditional expression.

Patent Literature 2 states that it provides a method and apparatus capable of performing various kinds of spatial conversion processing such as image deformation, linear spatial filtering, and luminance distribution correction without increasing the number of parameters or the processing load. Further, Patent Literature 2 also describes image processing for LBP (Local Binary Pattern) images and edge extracted images, in addition to luminance images.

Patent Literature 1

Japanese Patent Kokai Publication No. JP-P2007-48000A

Patent Literature 2

Japanese Patent Kokai Publication No. JP-P2011-86265A

SUMMARY

The disclosure of each Patent Literature cited above is incorporated herein in its entirety by reference thereto. The following analysis is given by the present inventors.

As described above, fingerprint is effective biological information for person identification. The quality of a latent fingerprint, however, can be an issue when it is used as a means of investigation. Normally, a fingerprint image from a latent fingerprint is of low quality, containing a lot of noise. As a result, noise removal processing is often applied to a fingerprint image from a latent fingerprint before this fingerprint image is compared with fingerprint images in a database.

In fingerprint matching, ridges constituting a fingerprint image and characteristic points constituted by endpoints and bifurcation points of the ridges are often used as information characterizing the fingerprint image. In this case, any information excluding the ridges and the characteristic points is treated as noise, and when a fingerprint image contains noise, processing that removes such noise is required.

For instance, if ridge extraction processing is applied to a fingerprint image shown in FIG. 21A, a ridge structure shown in FIG. 21B may be extracted. In FIG. 21B, white spots (white areas) included in areas 401 and 402, indicated by dotted circles in FIG. 21A, are treated as bifurcation points of a ridge and two ridges 411 and 412 extending from these bifurcation points are extracted. When ridges are extracted from the fingerprint image shown in FIG. 21A, however, it is expected that a ridge structure shown in FIG. 21C is extracted. In other words, the white spots included in the areas 401 and 402 shown in FIG. 21A are indeed sweat gland pores, not bifurcation points of a ridge, and these sweat gland pores prevent accurate extraction of ridges. Further, FIG. 21A includes a plurality of sweat gland pores, in addition to the white spots in the areas 401 and 402, and these sweat gland pores cause the extraction of the ridge structure shown in FIG. 21B. As described, since sweat gland pores on ridges prevent accurate extraction of ridges, it is desirable that sweat gland pores be regarded as noise superimposed on a fingerprint image and be removed.

In order to treat sweat gland pores in a fingerprint image as noise and remove them, the presence of sweat gland pores must be accurately recognized. If sweat gland pores on ridges can be accurately recognized, noise can be removed by erasing areas of recognized sweat gland pores. Here, if an expert familiar with fingerprint images sees the fingerprint image shown in FIG. 21A, he or she can relatively easily determine that the white spots in the areas 401 and 402 are sweat gland pores. It is, however, difficult to have an algorithm relating to image processing by a computer determine that the white spots in the areas 401 and 402 are sweat gland pores.

Hypothetically, even in image processing using a computer, if ridges are accurately extracted, white spots on the extracted ridges can be determined to be sweat gland pores. In order to accurately extract ridges, however, image processing such as removing sweat gland pores is required. In other words, a so-called "chicken and egg" situation occurs: in order to remove sweat gland pores in a fingerprint image, sweat gland pores must be extracted before extracting ridges; in order to extract sweat gland pores, ridges must be extracted first.

This kind of problem may occur in the technology disclosed in Patent Literature 1. In the technology disclosed in Patent Literature 1, ridge directions are extracted before extracting sweat gland pores. The extraction of ridge directions, however, should presume the accurate extraction of ridges themselves, and a ridge structure extracted before sweat gland pores are removed from a fingerprint image may contain an error.

Further, depending on the circumstances in which a fingerprint was acquired, there is a problem that each area constituting the fingerprint image has different noise superimposed. For instance, there could be a fingerprint image having a lot of sweat gland pores on ridges in an area A, but having very few sweat gland pores on ridges in an area B. The characteristic of such a fingerprint image cannot be uniformly determined. More concretely, the characteristic of the aforementioned fingerprint image cannot be determined as having "many sweat gland pores" focusing on the characteristic of the area A, or as having "few sweat gland pores" focusing on the characteristic of the area B. More details will be described later, but this is because if processing for removing sweat gland pores is performed on the entire fingerprint image in response to the characteristic of the area A, the quality of the area B, where very few sweat gland pores exist, will suffer. In other words, it is desirable that the characteristic of each area constituting an image be identified individually.

It is an object of the present invention to provide an image processing apparatus, image processing method and program that identify characteristic of each local area in an image.

According to a first aspect of the present invention, there is provided an image processing apparatus comprising an input unit that receives an image; a characteristic amount calculation unit that calculates an image characteristic amount characterizing a texture of a local area of the image received by the input unit; a characteristic amount vector calculation unit that calculates a first characteristic amount vector corresponding to the local area from the image characteristic amount; and a characteristic identification unit that identifies a characteristic of the local area on the basis of the first characteristic amount vector and a second characteristic amount vector calculated by the same method as the first characteristic amount vector and calculated from an image whose characteristic has been determined in advance.

According to a second aspect of the present invention, there is provided an image processing method comprising receiving an image; calculating an image characteristic amount characterizing a texture of a local area of the received image; calculating a first characteristic amount vector corresponding to the local area from the image characteristic amount; and identifying a characteristic of the local area on the basis of the first characteristic amount vector and a second characteristic amount vector calculated by the same method as the first characteristic amount vector and calculated from an image whose characteristic has been determined in advance.

According to a third aspect of the present invention, there is provided a program having a computer that controls an image processing apparatus execute a process of receiving an image; a process of calculating an image characteristic amount characterizing a texture of a local area of the received image; a process of calculating a first characteristic amount vector corresponding to the local area from the image characteristic amount; and a process of identifying a characteristic of the local area on the basis of the first characteristic amount vector and a second characteristic amount vector calculated by the same method as the first characteristic amount vector and calculated from an image whose characteristic has been determined in advance.

Further, this program can be stored in a computer-readable storage medium. The storage medium can be a non-transient one such as semiconductor memory, hard disk, and magnetic/optical storage medium. The present invention can be realized as a computer program product.

According to each aspect of the present invention, there is provided an image processing apparatus, image processing method and program that contribute to identifying characteristic of each local area of an image.

BRIEF DESCRIPTION OF DRAWINGS

FIG. 4 is a drawing showing an example of a relation between characteristics of local blocks and the names thereof.

FIG. 7 is a drawing for explaining an operation of the characteristic amount calculation unit to calculate an LBP value.

FIG. 8 is a drawing showing an example of a histogram calculated by the characteristic amount calculation unit.

FIG. 9 is a drawing showing an example of information outputted by a characteristic amount vector calculation unit.

FIG. 10 is an example of an image characteristic database constructed in a storage unit.

FIG. 11 is a drawing showing an example of local area characteristic information outputted by a characteristic identification unit.

FIG. 19 is another example of the image characteristic database constructed in the storage unit.

PREFERRED MODES

First, an outline of an exemplary embodiment will be given. Note that drawing reference signs in the summary are given to each element as an example solely to facilitate understanding for convenience and the description of the summary is not intended to limit the present invention in any way.

As described above, it is desirable that the characteristic of each local area be identified for each local area of an image.

Figure 1:
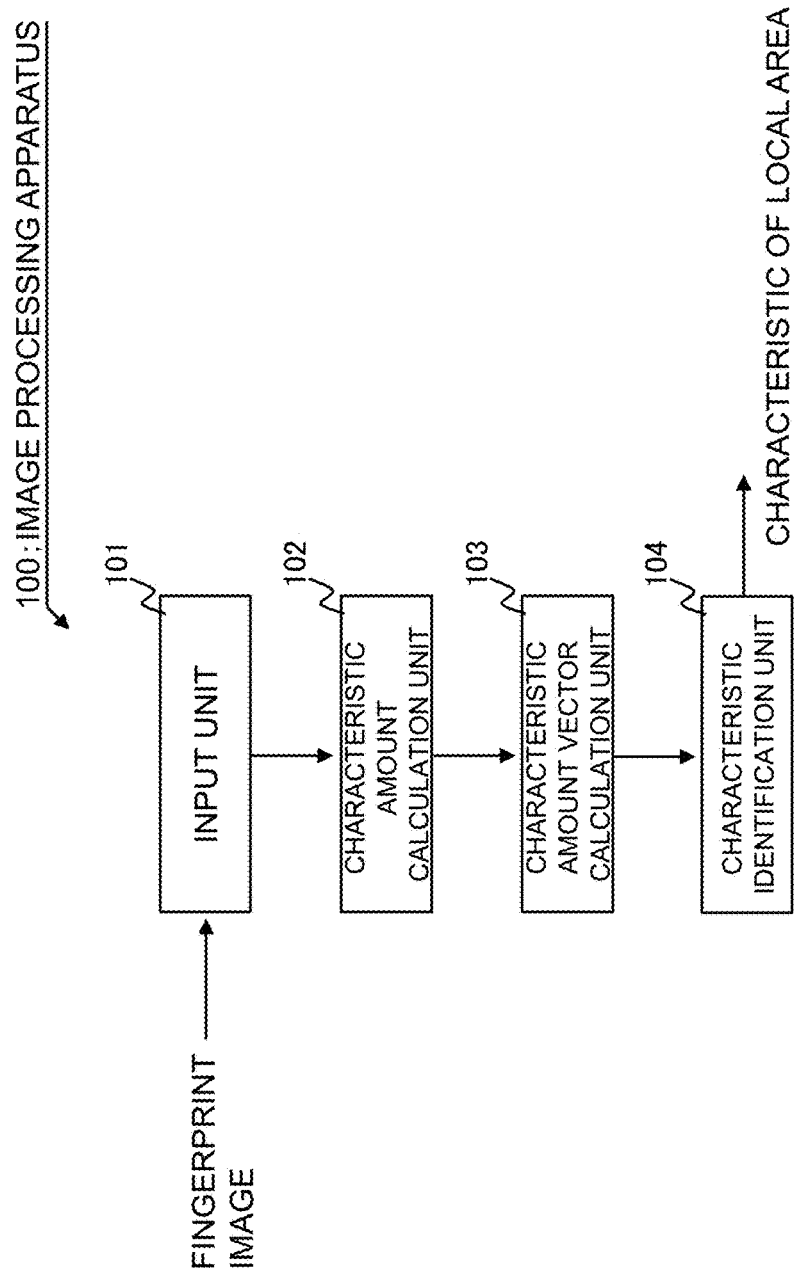
FIG. 1 is a drawing for describing an outline of an exemplary embodiment.

Therefore, there is provided an image processing apparatus 100 shown in FIG. 1 as an example. The information processing apparatus 100 comprises an input unit 101, a characteristic amount calculation unit 102, a characteristic amount vector calculation unit 103, and a characteristic identification unit 104. The input unit 101 receives an image. The characteristic amount calculation unit 102 calculates an image characteristic amount characterizing a texture of a local area of the image received by the input unit 101. The characteristic amount vector calculation unit 103 calculates a first characteristic amount vector corresponding to the local area from the image characteristic amount. The characteristic identification unit 104 identifies a characteristic of the local area on the basis of the first characteristic amount vector and a second characteristic amount vector calculated by the same method as the first characteristic amount vector and calculated from an image whose characteristic has been determined in advance.

The image processing apparatus 100 calculates an image characteristic amount indicating a local texture of a fingerprint image and quantifies the image characteristic amount in the format of the first characteristic amount vector. Further, the image processing apparatus 100 identifies a second characteristic amount vector similar to the first characteristic amount vector by calculating a similarity between the calculated first characteristic amount vector and the second characteristic amount vector calculated from an image having noise (such as sweat gland pores on ridges and faded ridges) superimposed thereon. Since the second characteristic amount vector is calculated from an image whose characteristic has been determined in advance and is associated with the characteristic of the image, the image processing apparatus 100 is able to identify the characteristic of the local area by identifying the second characteristic amount vector similar to the first characteristic amount vector. Note that texture in the present description includes surface texture expressed by at least the height or size of unevenness, a contrast width or a repetition period thereof, and a gradient orientation of similar luminances caused by a difference in the luminance value (pixel value) of each pixel constituting the input image.

Concrete exemplary embodiments will be described further in detail with reference to the drawings below. Note that the same signs are given to the same elements in each exemplary embodiment, and the explanation will be omitted.

[First Exemplary Embodiment]

A first exemplary embodiment will be described further in detail with reference to the drawings.

Figure 2:
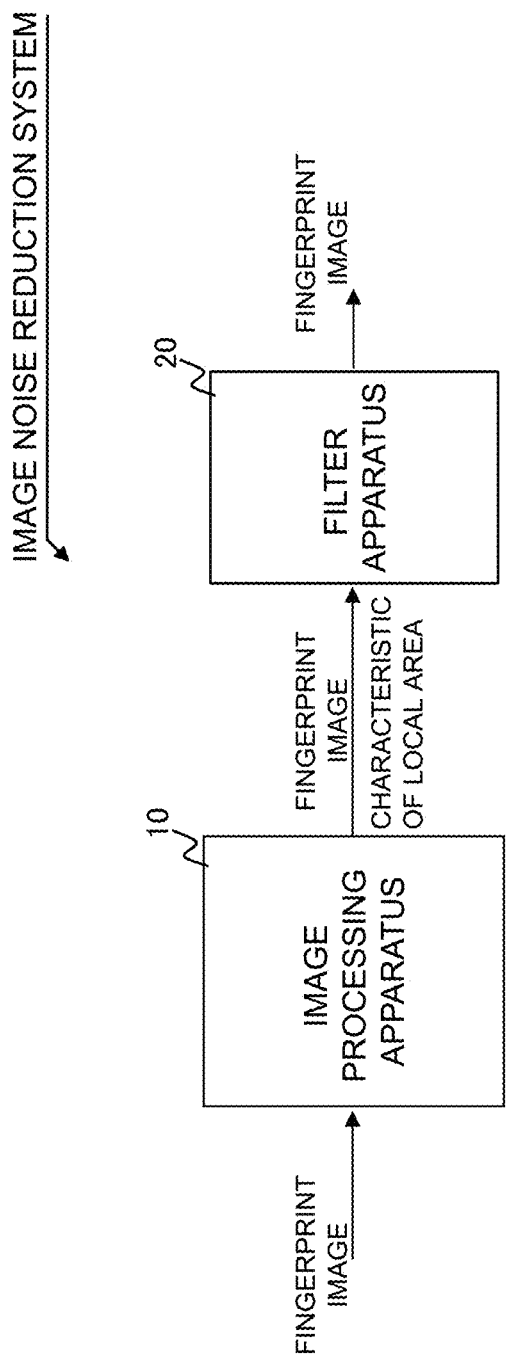
FIG. 2 is a drawing showing an example of an image noise reduction system relating to a first exemplary embodiment.

FIG. 2 is a drawing showing an example of an image noise reduction system relating to the first exemplary embodiment. In FIG. 2, the image noise reduction system is constituted by including an image processing apparatus 10 and a filter apparatus 20.

The image processing apparatus 10 receives a fingerprint image. The image processing apparatus 10 divides the input fingerprint image into a plurality of areas and identifies the characteristic of the divided local areas. For instance, the image processing apparatus 10 receives a fingerprint image having a size of 512 pixels by 512 pixels, and divides this fingerprint image into local blocks of 32 pixels by 32 pixels (refer to FIG. 3). In other words, the image processing apparatus 10 divides the input fingerprint image by 16 in both the vertical and horizontal directions.

The image processing apparatus 10 identifies the characteristic of each local block. For instance, since a local block 201 shown in FIG. 3 does not show any part of the fingerprint, the image processing apparatus 10 determines the characteristic of the local block 201 to be "no fingerprint." On the other hand, when there are many sweat gland pores on ridges in a local block 202, the image processing apparatus 10 determines the characteristic of the local block 202 to be "sweat gland pores." Further, when ridges in a local block 203 are recognized to be broken, the image processing apparatus 10 determines the characteristic of the local block 203 to be "faded."

As described, the image processing apparatus 10 identifies the characteristic of each local block constituting a fingerprint image. Further, in the first exemplary embodiment, a relationship between the characteristics of the local blocks and the names thereof is defined and explained as shown in FIG. 4. The characteristics of the local blocks treated by the image processing apparatus 10 are not, however, limited to the disclosure in FIG. 4. For instance, the characteristics of each local block identified by the image processing apparatus 10 may include wrinkles and pileous glands. Like sweat gland pores, wrinkles are indicated by white areas inside ridge pixels and may be mistaken as valley lines. Further, pileous glands are indicated by black areas inside valley pixels and may be mistaken as ridges. In other words, one can describe wrinkles and pileous glands as areas having the concentration values opposite to the concentration values they should have.

Here, out of the characteristics shown in FIG. 4, if "no fingerprint" and "fingerprint" are excluded, the characteristics of each local block the image processing apparatus 10 identifies can be considered to be noise superimposed on the input fingerprint image. Therefore, the image processing apparatus 10 can be regarded as an apparatus that identifies what kind of noise is superimposed on local blocks in a fingerprint image.

In FIG. 2, the image processing apparatus 10 outputs the fingerprint image and the characteristic of each local block constituting the fingerprint image to the filter apparatus 20. The filter apparatus 20 performs noise reduction processing (filter processing) on the fingerprint image on the basis of the characteristic of each local block acquired from the image processing apparatus 10. At this time, the filtering apparatus 20 applies processing suitable for each local block of the fingerprint image.

Figure 3:
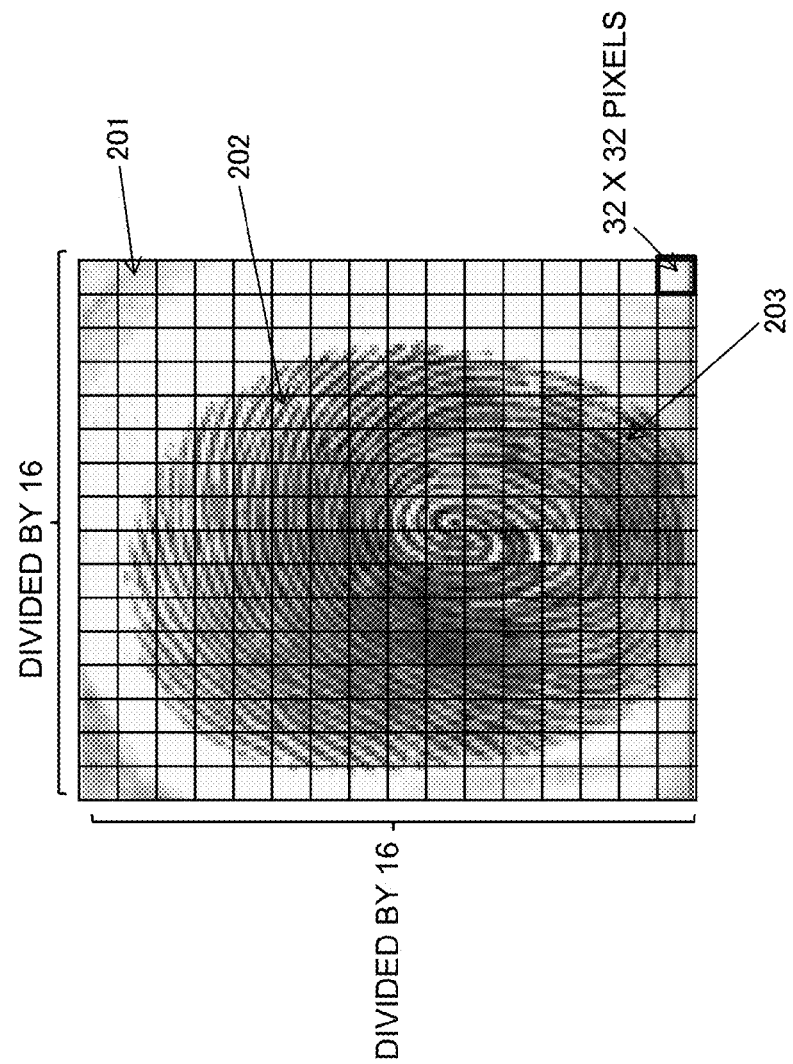
FIG. 3 is a drawing showing an example of a fingerprint image.

For instance, in FIG. 3, since the local block 202 has the characteristic relating to "sweat gland pores," the filtering apparatus 20 applies processing that removes sweat gland pores to the local block 202 of the fingerprint image. More concretely, the filtering apparatus 20 blurs the image of the local block 202 by averaging the pixel values of each pixel included in the local block 202 and neighboring pixels thereof. The sweat gland pores on ridges are removed by applying the blur processing to the local block 202.

Further, since the local block 203 shown in FIG. 3 has the characteristic relating to "faded," the filtering apparatus 20 applies processing that removes the "fadedness of ridges" to the local block 203 of the fingerprint image. More concretely, the filtering apparatus 20 performs processing that connects broken ridges in the local block 203. The filtering apparatus 20 outputs the fingerprint image to which the filter processing has been applied to an apparatus at a later stage (for instance, a characteristic extraction apparatus; not shown in the drawing).

Figure 5:
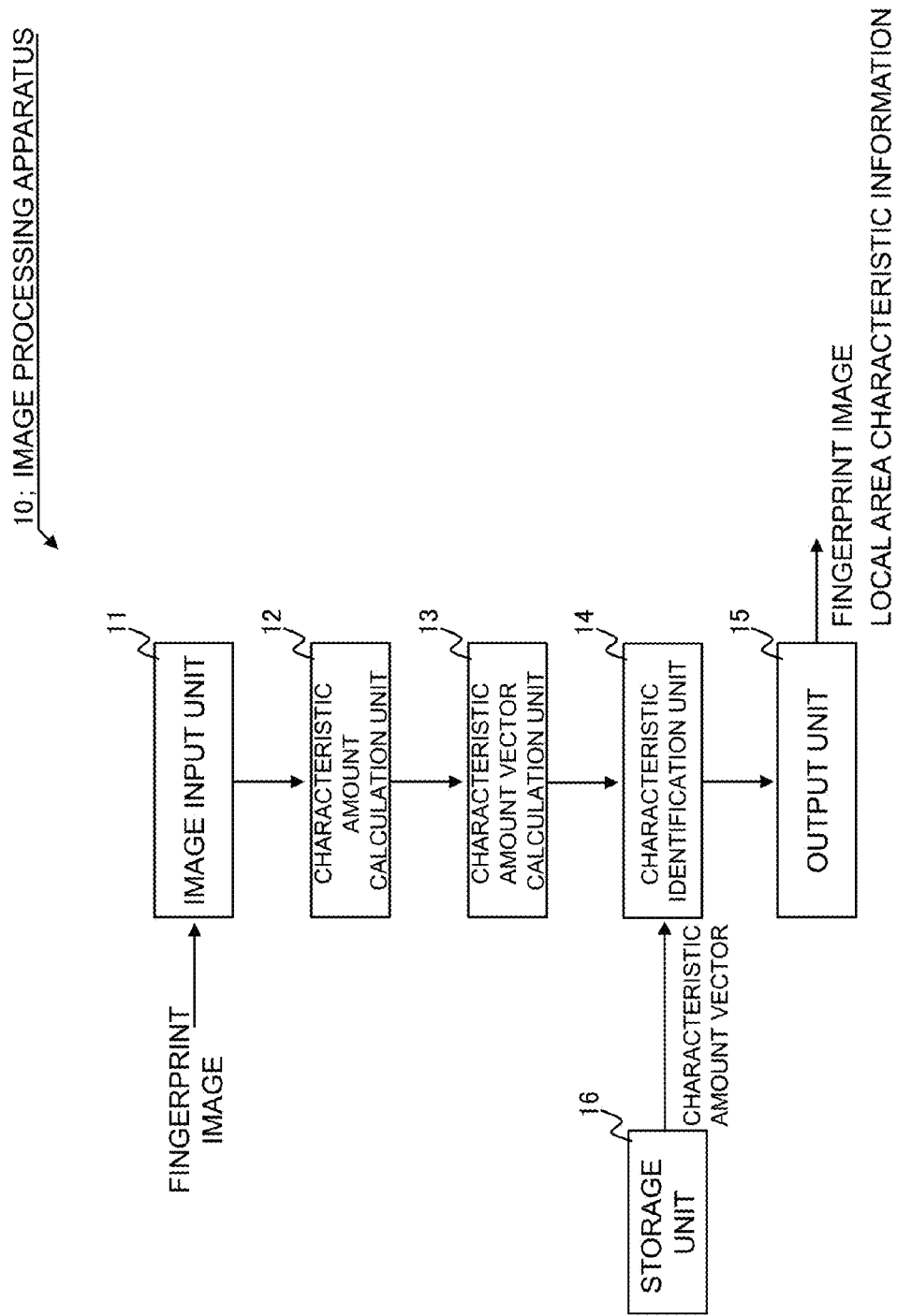
FIG. 5 is a drawing showing an example of an internal configuration of an image processing apparatus.

FIG. 5 is a drawing showing an example of the internal configuration of the image processing apparatus 10. In FIG. 5, the image processing apparatus 10 is constituted by including an image input unit 11, a characteristic amount calculation unit 12, a characteristic amount vector calculation unit 13, a characteristic identification unit 14, an output unit 15, and a storage unit 16 constituted by a storage medium such as a hard disk.

The image input unit 11 receives a fingerprint image. More concretely, the image input unit 11 receives image data stored in an external storage device such as a USB (Universal Serial Bus) memory device as a fingerprint image. Or the image input unit 11 may receive a fingerprint image via a network. Or the image input unit 11 may be given a scanner function, receiving a fingerprint image by taking a photograph of the fingerprint. Further, the input fingerprint image should be a grayscale image having the luminance value of each pixel expressed in 8 bits (0 to 255). The format of the input fingerprint image (image gradation, color format, etc.), however, is not limited thereto, and for instance the fingerprint image may be a color image. Further, the first exemplary embodiment will be described assuming that the size of the fingerprint image is 512 pixels by 512 pixels, but the size of the fingerprint image is not limited thereto. It goes without saying that the fingerprint image can be any size. The image input unit 11 outputs the acquired fingerprint image to the characteristic amount calculation unit 12.

The characteristic amount calculation unit 12 is means for calculating an image characteristic amount characterizing the texture of a local area of the input image (fingerprint image) received by the image input unit 11. More concretely, the characteristic amount calculation unit 12 divides the fingerprint image by a predetermined size and calculates an image characteristic amount characterizing the texture of each divided area (local area). In the first exemplary embodiment, the characteristic amount calculation unit 12 calculates an LBP (Local Binary Pattern) as the image characteristic amount of each local area.

Figure 6B:
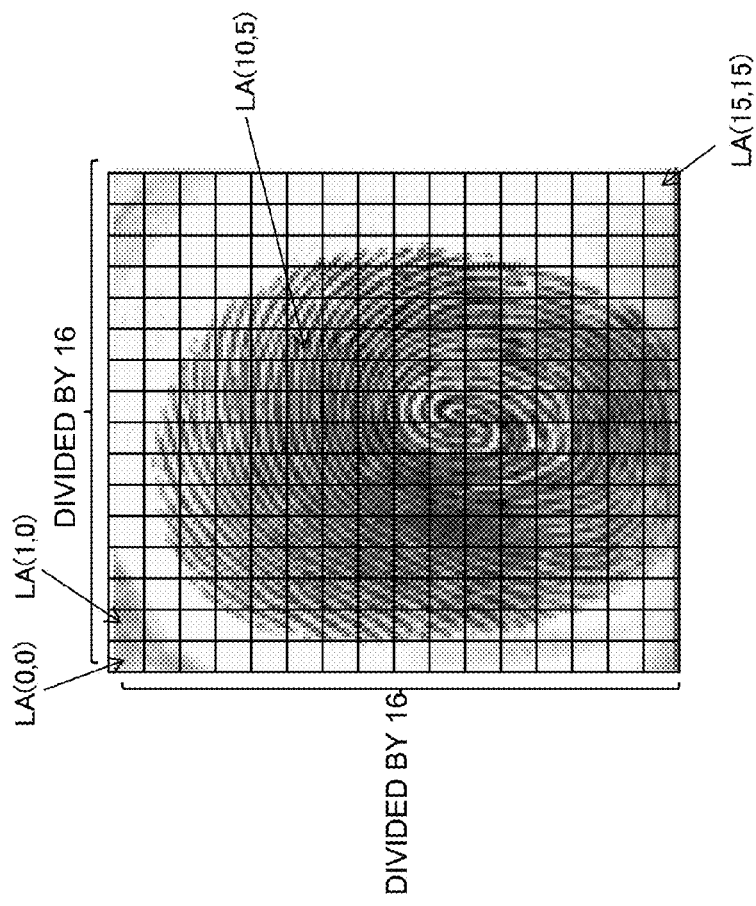
FIGS. 6A and 6B are drawings for explaining an operation of a characteristic amount calculation unit to calculate an image characteristic amount.
Figure 6A:
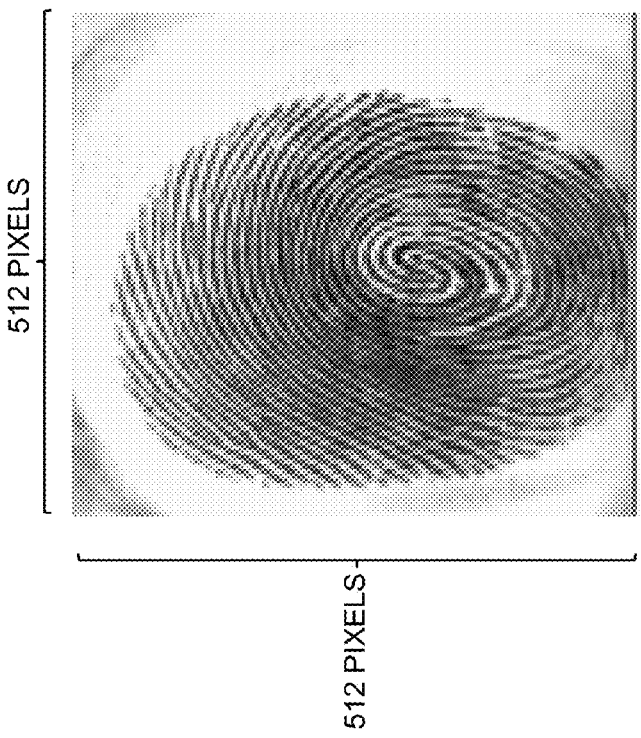

For instance, the characteristic amount calculation unit 12 divides a fingerprint image of 512 pixels by 512 pixels, such as one shown in FIG. 6A, by 16 in both the vertical and horizontal directions (refer to FIG. 6B). Each divided area becomes a local area (LA). In FIG. 6B and the drawings thereafter, the location of a local area is expressed by LA (X, Y) (where X and Y are integers in the range of 0≤X and Y≤15).

Note that the number used by the characteristic amount calculation unit 12 to divide a fingerprint image is not limited to 16. It may be greater or less than 16. Further, the fingerprint image may be divided by different numbers in the vertical and horizontal directions. For instance, it may be divided by 16 in the vertical direction and by 32 in the horizontal direction.

The characteristic amount calculation unit 12 calculates an LBP characteristic amount for each local area shown in FIG. 6B. When calculating the LBP characteristic amount, the characteristic amount calculation unit 12 calculates a LBP value from the pixel values of the pixels constituting the fingerprint image. The characteristic amount calculation unit 12 calculates the LBP value by setting the pixel for which an LBP value is calculated as a center pixel and comparing the pixel value (luminance value) of the center pixel with that of the comparison pixel thereof. More concretely, when the pixel value of the center pixel is not greater than the pixel value of the comparison pixel, the characteristic amount calculation unit 12 assigns "0" to the comparison pixel. On the other hand, when the pixel value of the center pixel is greater than the pixel value of the comparison pixel, the characteristic amount calculation unit 12 assigns "1" to the comparison pixel.

The characteristic amount calculation unit 12 assigns "0" or "1" to each comparison pixel, and arrange the calculated numbers, starting from a predetermined comparison pixel (for instance the upper left pixel viewed from the center pixel). A sequence of the arranged numbers becomes an LBP value.

Figure 7:
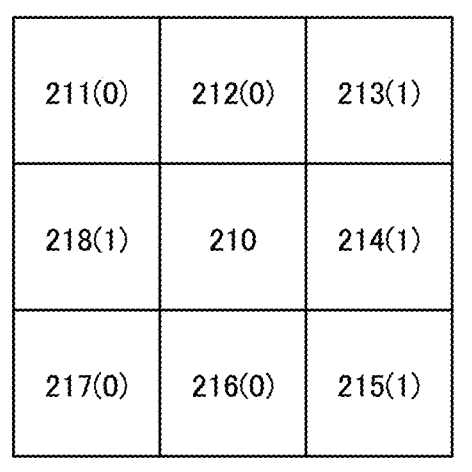

For instance, how the LBP value of a center pixel 210 shown in FIG. 7 is calculated will be described. Note that the numbers in parentheses in FIG. 7 denote values (0 or 1) obtained in the processing for comparing pixel values by the characteristic amount calculation unit 12. For instance, the characteristic amount calculation unit 12 compares the pixel value of a comparison pixel 211 with the pixel value of the center pixel 210 and stores the result thereof, "0." The characteristic amount calculation unit 12 repeats the same processing on comparison pixels 212 to 218. As a result, the comparison pixels 211 to 218 are encoded into 00111001 (57 in decimal). The characteristic amount calculation unit 12 sets the encoded value as the LBP value of the center pixel 210 (the LBP value of the center pixel 210 is 57 in the example above).

When the number of comparison pixels is P (8 in the above example) and the number of pixels that corresponds to the distance between a comparison pixel and the center pixel is R (1 in the above example), $LBP_{P,R}$ can be calculated by the following expression (1).

$$LBP_{P,R} = \sum_{p=0}^{P-1} s(g_P - g_c)2^P, \quad s(x) = \begin{cases} 1, & x \geq 0 \\ 0, & x < 0 \end{cases} \quad (1)$$

Further, $g_c$ denotes the pixel value of the center pixel, p denotes the order of the comparison pixels, and $g_p$ denotes the pixel value of the pth comparison pixel. When the LBP value of a pixel located on a boundary of a fingerprint image is calculated, the characteristic amount calculation unit 12 may set the pixel value of a pixel that does not exist in advance and utilize it to calculate the LBP value.

Here, for instance, let's consider a case where the LBP value of each pixel is calculated from two fingerprint images, a fingerprint image A and a fingerprint image B. In this case, even when the fingerprint images A and B have approximately the same texture, the LBP values calculated from these images will be greatly different from each other if the fingerprint image B is slightly tilted in relation to the fingerprint image A. In order to solve such an inconvenience, it is desirable that the LBP value actually be calculated using a technique called rotation—invariant uniform LBP. That is, it is desirable that LBP values be calculated while the positions of the comparison pixels are sequentially rotated, and that the minimum value from a plurality of obtained LBP values be selected as the LBP value of the center pixel. In the first exemplary embodiment, however, LBP values calculated by the expression (1) are used assuming that there is no tilting between fingerprint images to facilitate understanding. Therefore, the range of the LBP values will be 0 to 255.

Further, an LBP image can be obtained by replacing the pixel value of each pixel in the fingerprint image received by the image processing apparatus 10 with the LBP value calculated by the characteristic amount calculation unit 12. It can also be understood as conversion of the input fingerprint image into an LBP image inside the image processing apparatus 10.

The characteristic amount calculation unit 12 calculates an LBP characteristic amount for each local area after having calculated the LBP value of each pixel constituting the fingerprint image.

The characteristic amount calculation unit 12 calculates the LBP characteristic amount corresponding to each local area from the LBP value (the pixel value of the LBP image) of each pixel constituting the fingerprint image. Since the fingerprint image has a size of 512 pixels by 512 pixels and it is divided by 16 in both the vertical and horizontal directions, one local area includes 1024 pixels (512/16=32; 32×32=1024). In other words, 1024 LBP values are obtained from a local area.

The characteristic amount calculation unit 12 determines predetermined ranges of LBP values and generates classes. Next, the characteristic amount calculation unit 12 counts the number of LBP values belonging to each class. The number of LBP values counted for each class becomes frequency. For instance, when classes are generated by dividing the range of LBP values (0 to 255) by eight, a relationship between class and frequency (histogram) shown in FIG. 8 can be obtained. The histogram shown in FIG. 8 is the LBP characteristic amount characterizing the texture of each local area constituting the fingerprint image. The characteristic amount calculation unit 12 hands over the information (histogram) of the LBP characteristic amount of each local area to the characteristic amount vector calculation unit 13.

The characteristic amount vector calculation unit 13 is means for calculating a characteristic amount vector (the first characteristic amount vector) corresponding to each local area from the LBP characteristic amount calculated by the characteristic amount calculation unit 12. More concretely, the characteristic amount vector calculation unit 13 calculates the characteristic amount vector by selecting a predetermined class from the classes in the histogram and regarding the frequency belonging to the selected class as an element. In the first exemplary embodiment, the characteristic amount vector calculation unit 13 calculates the characteristic amount vector by arranging the number (frequency) of LBP values counted for each class in order. For instance, in the example shown in FIG. 8, a characteristic amount vector FV expressed by the following expression (2) is calculated.

$$FV = \{a1, a2, \ldots, a7, a8\} \quad (2)$$

Note that the range of LBP values is divided into eight classes in the example of FIG. 8. Therefore, the characteristic amount vector calculation unit 13 calculates an eight-dimensional characteristic amount vector. Further, the characteristic amount vector calculation unit 13 may calculate a characteristic amount vector having a degree different from the class number of the histogram used by the characteristic amount calculation unit 12 to calculate the LBP characteristic amount. In other words, all the classes of the LBP characteristic amount do not necessarily contribute to characterizing the texture of a local area. Therefore, the characteristic amount vector calculation unit 13 may decide not to use a class and the frequency thereof that do not contribute to characterizing a local area as an element of the characteristic amount vector and may reduce the degree of the characteristic amount vector.

After completing the calculation of the characteristic amount vector for each local area, the characteristic amount vector calculation unit 13 associates location information of each local area with the characteristic amount vector thereof and outputs the result to the characteristic identification unit 14. More concretely, the characteristic amount vector calculation unit 13 outputs information (local area location, corresponding characteristic amount vector FV) shown in FIG. 9 to the characteristic identification unit 14. Note that the corresponding characteristic amount vector FV is represented by FV (X, Y) using X and Y used for indicating the location of a local area in FIG. 9.

The characteristic identification unit 14 is means for identifying the characteristic of each local area on the basis of the characteristic amount vector (the first characteristic amount vector) calculated by the characteristic amount vector calculation unit 13 and a characteristic amount vector (the second characteristic amount vector) calculated by the same method as the first characteristic amount vector and calculated from an image whose characteristic has been determined in advance. At this time, the characteristic identification unit 14 utilizes information stored in the storage unit 16.

The storage unit 16 has the characteristic of an image whose characteristic has been determined in advance associated with a characteristic amount vector calculated from this image and stores this information. More concretely, in the storage unit 16, an image characteristic database that associates a specific characteristic possessed by an image with a characteristic amount vector calculated from the image having this specific characteristic and stores this information is constructed.

FIG. 10 is an example of the image characteristic database constructed in the storage unit 16. Note that the image characteristic database shown in FIG. 10 is constructed in advance before the image processing apparatus 10 starts to operate.

The image characteristic database is constructed as follows.

First, an administrator of the image noise reduction system prepares a fingerprint image having a characteristic texture. More concretely, the administrator prepares a fingerprint image having the characteristic that the image processing apparatus 10 is trying to judge. For instance, the administrator prepares a fingerprint image having sweat gland pores on ridges or a fingerprint image having faded ridges.

Next, the administrator divides the prepared fingerprint image in the same way as the characteristic amount calculation unit 12 divides a fingerprint image, and creates a group of local areas out of the fingerprint image.

Next, a person with expertise in fingerprint images (referred to as "expert" hereinafter) determines a characteristic possessed by each local area of the fingerprint image. For instance, when many sweat gland pores are seen on ridges in one local area, the characteristic of this local area is classified into "sweat gland pores."

Next, the administrator has a computer perform the processing described as the operation of the characteristic amount calculation unit 12 and the characteristic amount vector calculation unit 13 on the local areas the characteristics of which have been judged by the expert, and obtains characteristic amount vectors corresponding to these local areas.

The administrator associates the obtained characteristic amount vectors with the characteristics of the local areas judged by the expert and registers the result in the image characteristic database. By repeatedly associating prepared fingerprint images with the calculation of characteristic amount vectors and the characteristics judged by the expert for all the local areas of the fingerprint images, the image characteristic database shown in FIG. 10 can be constructed.

For each local area of the fingerprint image, the characteristic identification unit 14 identifies a characteristic possessed by each local area on the basis of the similarity between the corresponding characteristic amount vector and the characteristic amount vectors stored in the image characteristic database.

More concretely, the characteristic identification unit 14 sets the characteristic amount vector of a local area calculated from the fingerprint image as a characteristic amount vector on an inquiry side and sets a characteristic amount vector stored in the image characteristic database as a characteristic amount vector on a registration side. The characteristic identification unit 14 calculates the chi-squared distance as an index for measuring the similarity between these two characteristic amount vectors. More concretely, the characteristic identification unit 14 calculates the chi-squared distance using the following expression (3).

$$\text{Chi-squared distance} = \sum_i (H1(i) - H2(i))^2 / H2(i) \quad (3)$$

Further, H1 and H2 denote two histograms to be compared, and i is the bin index in the histograms.

Next, the characteristic identification unit 14 identifies a characteristic amount vector (characteristic amount vector stored in the image characteristic database) on the registration side having the minimum chi-squared distance value among the calculated chi-squared distances. The characteristic identification unit 14 sets the characteristic associated with this identified characteristic amount vector as the characteristic of the local area corresponding to the characteristic amount vector on the inquiry side.

For instance, let's consider a case where the characteristic identification unit 14 identifies the characteristic of a local area LA (10, 5) shown in FIG. 6B. In this case, the characteristic identification unit 14 calculates the chi-squared distances between a characteristic amount vector FV (10, 5) of the local area LA (10, 5) and each of characteristic amount vectors FV1-1, FV1-2, . . . , FV2-1, FV2-2, . . . stored in the image characteristic database.

If the chi-squared distance between the characteristic amount vector FV (10, 5) and the characteristic amount vector FV3-1 is the smallest among the calculated chi-squared distances, the characteristic identification unit 14 sets the characteristic of the local area LA (10, 5) to "sweat gland pores." On the other hand, if the chi-squared distance between the characteristic amount vector FV (10, 5) and the characteristic amount vector FV4-1 is the smallest among the calculated chi-squared distances, the characteristic identification unit 14 sets the characteristic of the local area LA (10, 5) to "faded."

After identifying the characteristic of each local area, the characteristic identification unit 14 calculates local area characteristic information regarding local area locations and the corresponding characteristics, and outputs the information to the output unit 15. More concretely, the characteristic identification unit 14 outputs information shown in FIG. 11 (local area locations and the corresponding characteristics) to the output unit 15 as the local area characteristic information.

The output unit 15 outputs the fingerprint image received by the image input unit 11 and the local area characteristic information calculated by the characteristic identification unit 14 to the filter apparatus 20. Note that the filter apparatus 20 may receive the data (the fingerprint image and the local area characteristic information) from the output unit 15 in any form. For instance, the data may be received using an external storage device or via a network.

Figure 12:
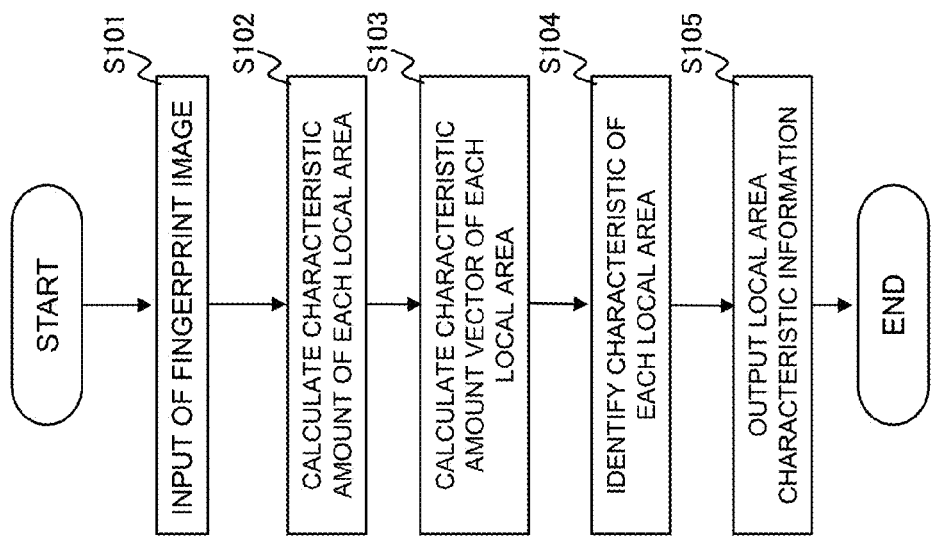
FIG. 12 is a flowchart showing an example of an operation of the image processing apparatus.

FIG. 12 is a flowchart showing an example of the operation of the image processing apparatus 10. In FIG. 12, the image processing apparatus 10 first receive a fingerprint image (step S101).

Next, the image processing apparatus 10 divides the fingerprint image into a predetermined size and calculates the image characteristic amount for each divided area (local area) (step S102).

Then, from the characteristic amount of each local area, the image processing apparatus 10 calculates the characteristic amount vector by quantifying the texture of each local area (step S103).

Next, the image processing apparatus 10 identifies a characteristic possessed by each local area on the basis of the characteristic amount vector corresponding to each local area and the characteristic amount vectors stored in the storage unit 16 (step S104).

Then, the image processing apparatus 10 outputs the local area characteristic information that defines the relations between the locations of the local areas and the corresponding characteristics to an external apparatus (for instance the filter apparatus 20) (step S105).

Next, the filter apparatus will be described.

Figure 13:
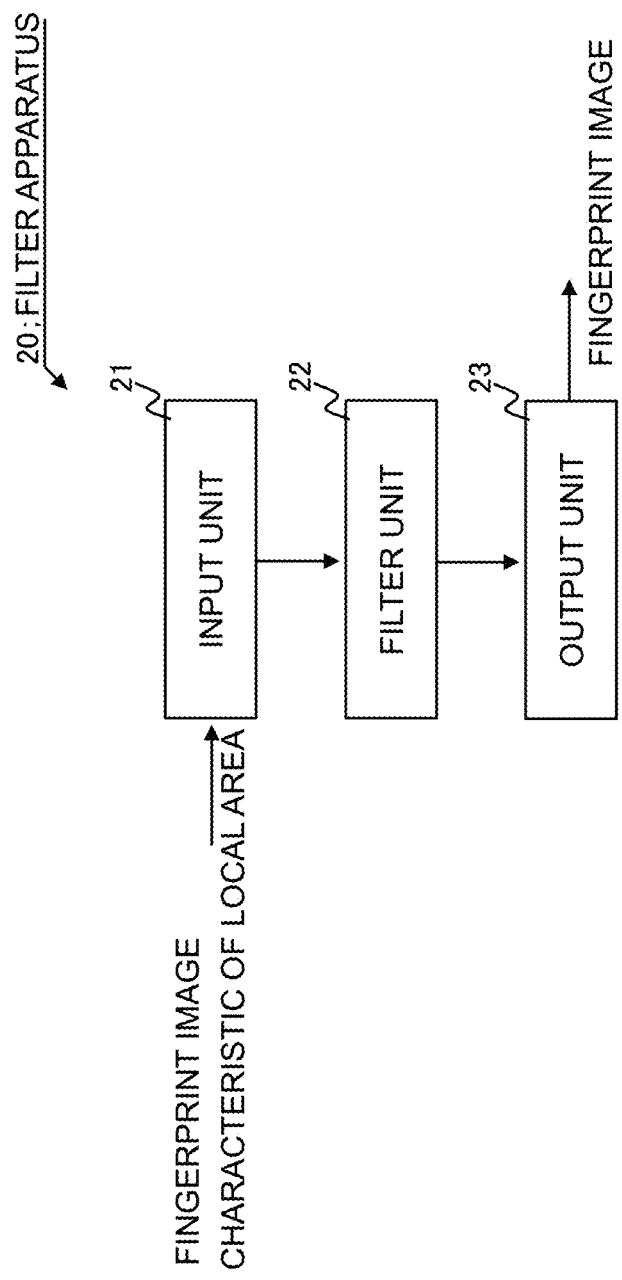
FIG. 13 is a drawing showing an example of an internal configuration of a filter apparatus relating to the first exemplary embodiment.

FIG. 13 is a drawing showing an example of the internal configuration of the filter apparatus 20. In FIG. 13, the filter apparatus 20 is constituted by including an input unit 21, a filter unit 22, and an output unit 23.

The input unit 21 receives the fingerprint image and the local area characteristic information outputted by the image processing apparatus 10. The input unit 21 hands over the acquired information to the filter unit 22.

The filter unit 22 performs image processing on the fingerprint image on the basis of the local area characteristic information. At this time, the filter unit 22 applies processing (filter processing) to each local area of the fingerprint image with a size of a local area matched between the image processing apparatus 10 and the filter apparatus 20 as the unit.

For instance, let's assume that the filter unit 22 acquires the local area characteristic information shown in FIG. 11. In this case, since a local area LA (0, 0) of the fingerprint image is characterized as "no fingerprint," the filter unit 22 does not apply any processing to the local area LA (0, 0). Further, the filter unit 22 does not perform any processing on local areas characterized as, for instance, "fingerprint." This is because local areas having the characteristic "fingerprint" are areas showing the fingerprint without any noise.

The local area LA (10, 5) is characterized as "sweat gland pores." In this case, the filter unit 22 applies processing suitable for removing sweat gland pores on ridges to the local area LA (10, 5) of the fingerprint image. For instance, as described above, the filter unit 22 performs "blur processing" suitable for removing sweat gland pores on the local area LA (10, 5) of the fingerprint image.

After having applied image processing to each local area of the fingerprint image according to the characteristic thereof, the filter unit 22 hands over the fingerprint image to the output unit 23.

The output unit 23 outputs the fingerprint image to which the image processing suitable for each local area has been applied to an apparatus following the filter apparatus 20 (for instance a characteristic extraction apparatus; not shown in the drawing).

Here, the image processing apparatus 10 relating to the first exemplary embodiment does not have the "chicken and egg" problem that, when one determines a characteristic possessed by a fingerprint image, an accurate characteristic cannot be determined unless other pieces of information have already been known.

As described, ridges should be accurately extracted in order to determine the presence of sweat gland pores thereon, but the presence of sweat gland pores will prevent the accurate extraction of ridges. When determining the characteristic of an image, the image processing apparatus 10 identifies the characteristic of each local area of the fingerprint image by comparing the characteristic amount vector characterizing a local area and the characteristic amount vector generated from an image whose characteristic has been determined by an expert. Since it is possible to think that the two compared characteristic amount vectors are obtained by quantifying the textures of local areas, it can be said that the image processing apparatus 10 determines the characteristic of a local area by directly comparing the texture of the local area and the textures possessed by various images stored as reference information in the storage unit 16 in advance. Therefore, the image processing apparatus 10 does not have the so-called "chicken and egg" problem that, when one determines a characteristic possessed by a fingerprint image, an accurate characteristic cannot be determined unless other pieces of information have already been known.

Further, the image processing apparatus 10 is able to accurately identify the characteristic of a local area even when there is a difference in brightness between fingerprint images since it uses the LBP characteristic amount as the image characteristic amount of each local area constituting the fingerprint image. This is because the LBP characteristic amount cancels the effect of the brightness of the original image (fingerprint image) due to the calculation method thereof. In other words, even when the brightness of two fingerprint images differs due to differences in the circumstances in which these fingerprint images were acquired, the characteristic of a local area in the fingerprint image is accurately identified as long as the textures are similar.

Further, because the image processing apparatus 10 accurately identify the characteristic of each local area constituting a fingerprint image, it improves the quality of the resultant fingerprint image processed by the filter apparatus 20.

Figure 14B:
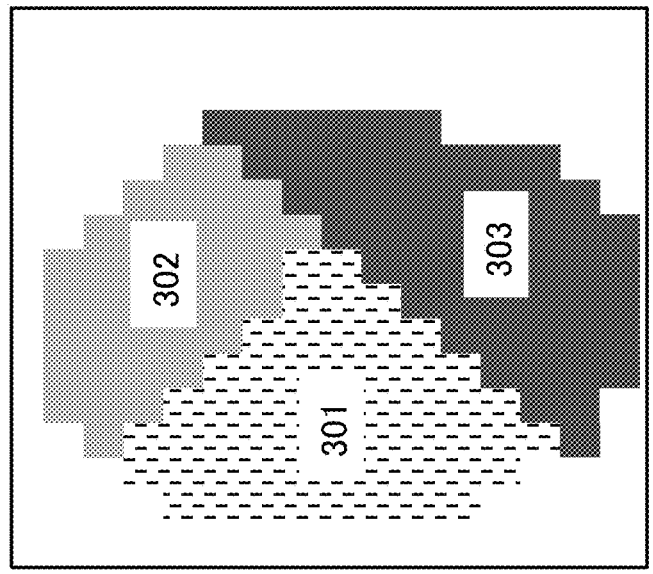
FIGS. 14A and 14B are drawings showing an example of a fingerprint image.
Figure 14A:

For instance, let's assume that we want to remove the noise superimposed on a fingerprint image shown in FIG. 14A. Let's assume that, in the fingerprint image shown in FIG. 14A, some areas do not have any noise superimposed, some areas have many sweat gland pores on ridges, and ridges in some areas are faded.

More concretely, in FIG. 14B, we'll assume that an area 301 does not have any noise superimposed (area having the characteristic relating to "fingerprint"), an area 302 has noise relating to "sweat gland pores," and an area 303 has noise relating to "fadedness." If no image processing is applied to the fingerprint image shown in FIG. 14B, the image quality of the areas 302 and 303 will remain low.

Therefore, let's assume that processing suitable for removing sweat gland pores will be applied to the entire fingerprint image. Then, the image quality of the area 302 may improve, but the image quality of the areas 301 and 303 may deteriorate. Since the area 301 originally has no noise superimposed, it is desirable that no processing be applied thereto. If, however, the processing suitable for removing sweat gland pores (for instance blur processing) is applied to the area 301, the outlines of ridges and characteristic points may be blurred and the ridge structure may be damaged. Further, since the area 303 has the noise relating to "fadedness," applying the processing suitable for removing sweat gland pores will not repair the fadedness of ridges.

As described, since noise superimposed on a fingerprint image varies widely, not only the noise cannot be removed, but also the image quality may deteriorate unless image processing suitable for the noise superimposed in each local area of the fingerprint image is applied. Or if all types of processing addressing the noise superimposed on the fingerprint image are mixed and blindly applied, side effects such as damaging a ridge structure in an area without noise can be expected.

Meanwhile, the image processing apparatus 10 relating to the first exemplary embodiment identifies the characteristic of a local area belonging to the area 301 as "fingerprint" out of each local area of the fingerprint image shown in FIG. 14A. Similarly, the image processing apparatus 10 identifies the characteristics of local areas belonging to the areas 302 and 303 as "sweat gland pores" and as "faded," respectively. The image processing apparatus 10 outputs local area characteristic information associating the areas 301, 302, and 303 with "fingerprint," "sweat gland pores," and "faded," respectively, to the filter apparatus 20. After receiving this local area characteristic information, the filter apparatus 20 is able to apply different processing suitable for each area, performing no processing on the area 301, processing suitable for removing sweat gland pores on the area 302, and processing suitable for repairing the fadedness of ridges on the area 303.

In other words, the filter apparatus 20 relating to the first exemplary embodiment is able to apply optimum processing for the noise superimposed on a particular area of the fingerprint image. As a result, the image noise reduction system relating to the first exemplary embodiment is able to improve the entire quality of the fingerprint image.

Figure 15A:
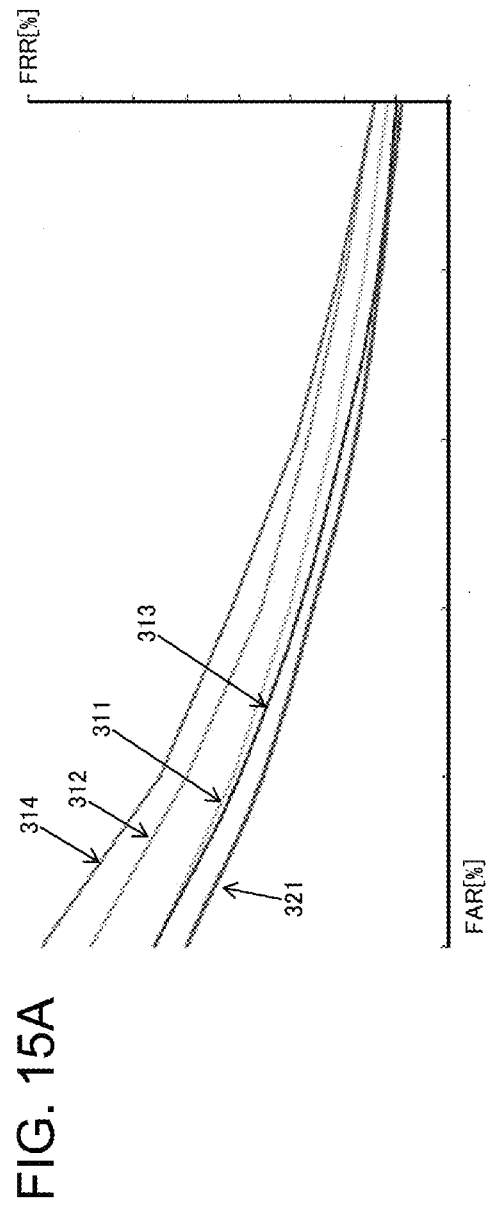
FIGS. 15A and 15B are drawings showing examples of receiver operating characteristic curves in fingerprint matching.
Figure 15B:
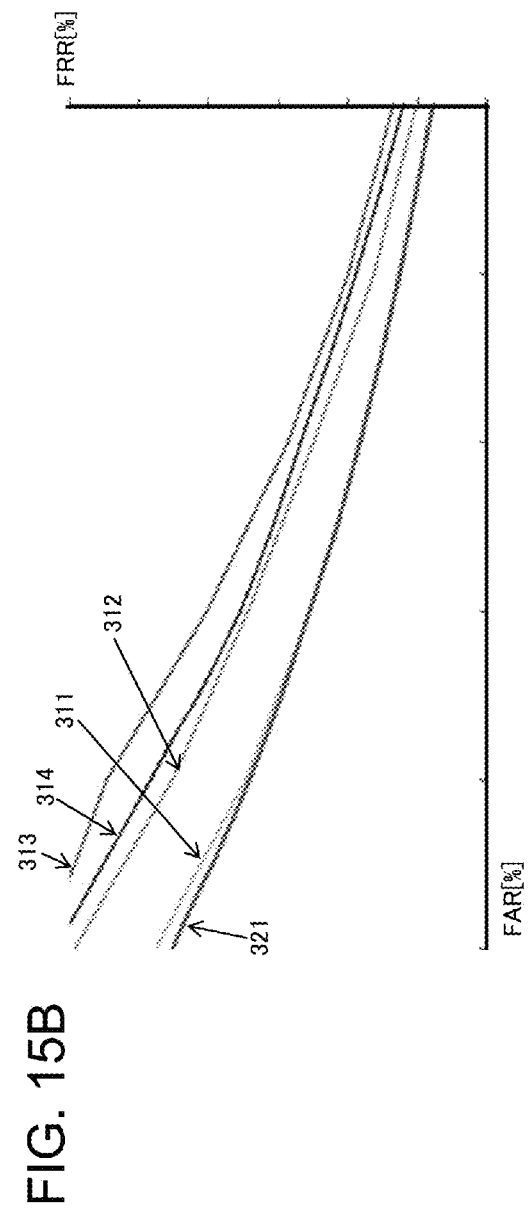

FIGS. 15A and 15B are drawings showing examples of receiver operating characteristic (ROC) curves in fingerprint matching. FIG. 15A is a simulation result of a case where fingerprint images on both inquiry and registration sides have a lot of noise relating to sweat gland pores superimposed on some of their areas. FIG. 15B is a simulation result of a case where the fingerprint images on both inquiry and registration sides have less noise relating to sweat gland pores than in the case of FIG. 15A. Note that having a lot of noise relating to sweat gland pores means that the area of ridges having sweat gland pores large enough that the matching result will be adversely affected is large, and having less noise relating to sweat gland pores means that the area of ridges having sweat gland pores large enough that the matching result will be adversely affected is small.

The vertical axes of the graphs in FIGS. 15A and 15B represents the false rejection rate (FRR), and the horizontal axes the false acceptance rate (FAR). In FIGS. 15A and 15B, the more the curves relating to the matching results incline toward the lower left, the higher the matching results.

A curve 311 in FIGS. 15A and 15B is the result of matching fingerprint images without applying any filter processing to the images on either the inquiry or registration side. A curve 312 is the result of matching fingerprint images when no filter processing is applied to the fingerprint images on the inquiry side, but "blur processing" suitable for removing sweat gland pores is applied to the fingerprint images on the registration side. A curve 313 is the result of matching fingerprint images when the "blur processing" is applied to the fingerprint images on the inquiry side, but no filter processing is applied to the fingerprint images on the registration side. A curve 314 is the result of matching fingerprint images when the "blur processing" is applied to the fingerprint images on both the inquiry and registration sides. A curve 321 is the result of matching fingerprint images when the filter processing by the filter apparatus 20 relating to the first exemplary embodiment is applied to the fingerprint images on both the inquiry and registration sides.

FIGS. 15A and 15B show that the matching results relating to the curve 321 are the most desirable in both the case with a lot of sweat gland pores (FIG. 15A) or the case with less sweat gland pores (FIG. 15B). This fact indicates that the quality of fingerprint images after the filter apparatus 20 relating to the first exemplary embodiment has performed the image processing (filter processing) on the fingerprint images on the inquiry and registration sides is the highest. This is because higher quality of fingerprint images improves the matching accuracy (the ROC curves incline toward the lower left in FIGS. 15A and 15B).

Further, referring to FIG. 15A, one can understand that the matching results of the curve 314 (the blur processing applied to the fingerprint images on both the inquiry and registration sides) are worse than those of the curve 311 (no filter processing applied to the fingerprint images on either the inquiry or the registration side). This indicates that, out of areas constituting fingerprint images, areas that do not require the blur processing (for instance areas without any noise superimposed) are larger than areas that do require the blur processing (areas having sweat gland pores). In other words, even if sweat gland pores on ridges in particular areas can be eliminated by applying the blur processing to the entire fingerprint image, the side effects of the blur processing will damage ridge structures in areas that do not require any blur processing and the matching results will deteriorate.

On the other hand, referring to FIG. 15B, one can understand that the matching results of the curves 311 and 321 show no significant difference. This is because there are few sweat gland pores on ridges included in the fingerprint images on the inquiry and registration sides, and applying the blur processing to areas having the noise relating to sweat gland pores superimposed thereon does not impact the matching results significantly.

The results shown in FIGS. 15A and 15B indicate that the filter apparatus 20 relating to the first exemplary embodiment improves the quality of an entire fingerprint image by applying optimum processing for the noise superimposed on a particular area of the fingerprint image.

As described, the image processing apparatus 10 relating to the first exemplary embodiment divides a fingerprint image and calculates an LBP characteristic amount (a histogram of LBP values) for each divided local area. The image processing apparatus 10 calculates a characteristic amount vector quantifying the texture of each local area from the histogram of the local area, and calculates the similarity to characteristic amount vectors generated from an image whose characteristic has been determined by an expert. The image processing apparatus 10 identifies the characteristic (i.e., texture) possessed by each local area on the basis of the calculated similarity. As a result, the image processing apparatus 10 is able to accurately identify the characteristic of each local area constituting the fingerprint image.

Further, the image noise reduction system relating to the first exemplary embodiment is able to obtain a high-quality fingerprint image by utilizing the local area characteristic information outputted by the image processing apparatus 10.

[Second Exemplary Embodiment]

Next, a second exemplary embodiment will be described in detail with reference to the drawings.

In the first exemplary embodiment, the local area characteristic information outputted by the image processing apparatus 10 is utilized for selecting the filter processing applied to a fingerprint image. In the second exemplary embodiment, other usage forms of the local area characteristic information will be described.

Figure 16:
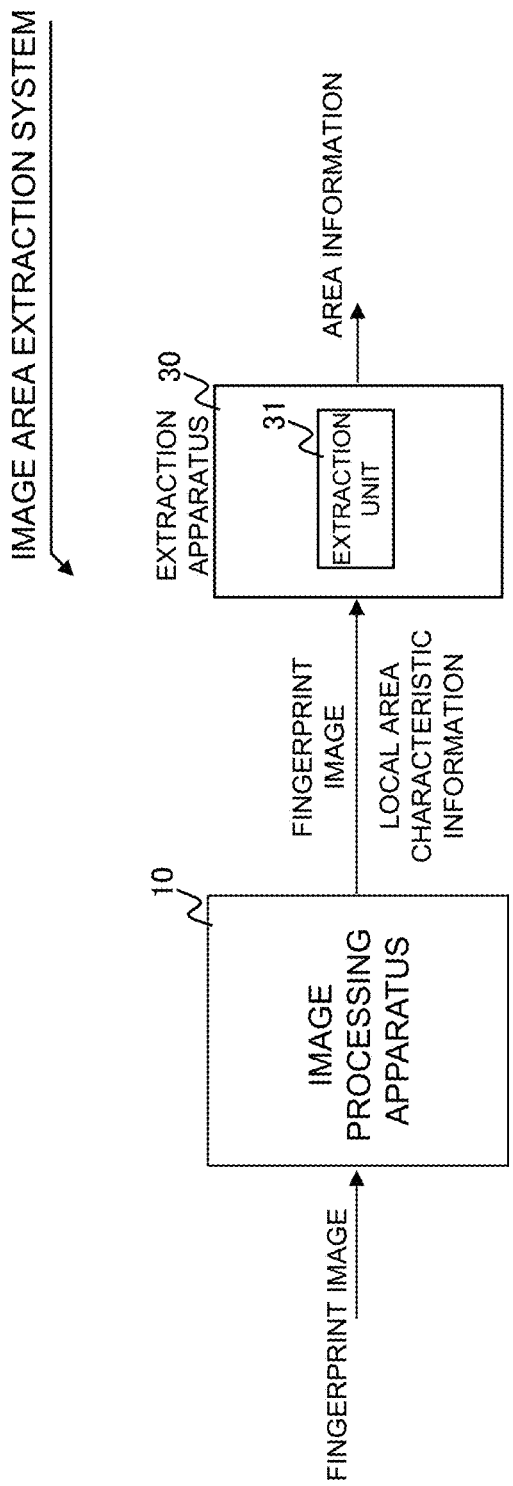
FIG. 16 is a drawing showing an example of an image area extraction system relating to a second exemplary embodiment.

For instance, as shown in FIG. 16, the image processing apparatus 10 outputs the fingerprint image and the local area characteristic information to an extraction apparatus 30. An extraction unit 31 of the extraction apparatus 30 is able to extract only a fingerprint by removing local areas having the characteristic "no fingerprint" from the fingerprint image using the local area characteristic information. For instance, the extraction unit 31 is able to extract the areas 301 to 303 shown in FIG. 14B from the fingerprint image.

Figure 17:
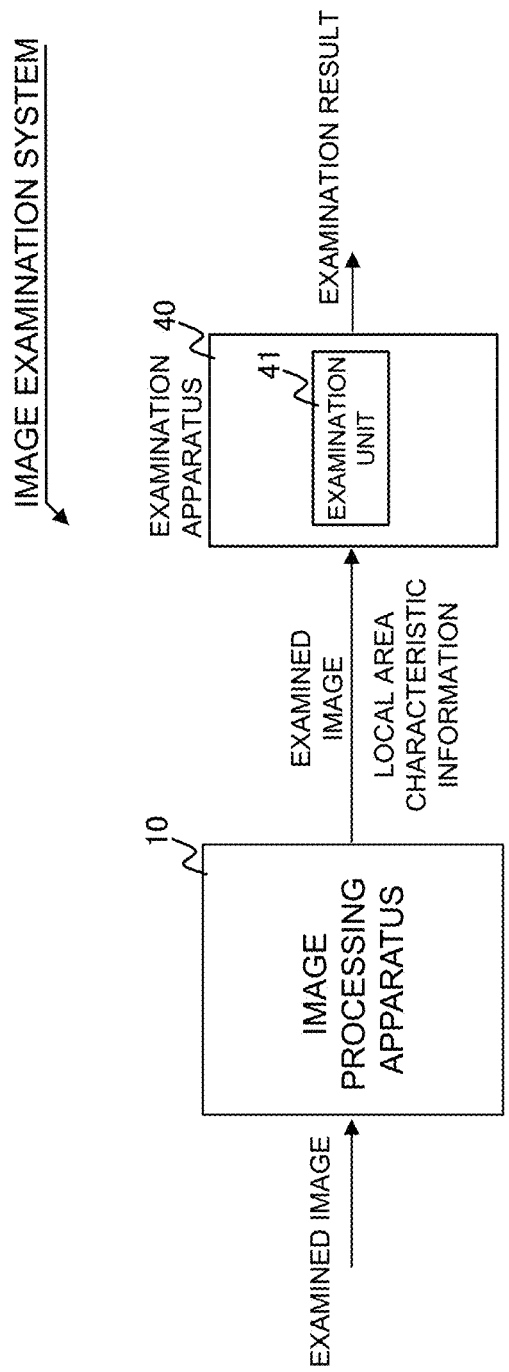
FIG. 17 is a drawing showing an example of an image examination system relating to the second exemplary embodiment.

Or as shown in FIG. 17, the image processing apparatus 10 receives an examined image. The examined image is an image subject to a judgment of whether or not it shows a fingerprint. The image processing apparatus 10 outputs the local area characteristic information regarding the examined image to an examination apparatus 40. At this time, the image processing apparatus 10 determines whether or not the examined image shows any fingerprint therein and includes the result in the local area characteristic information. More concretely, the characteristic amount vector of a fingerprint image with less noise is stored in the image characteristic database of the image processing apparatus 10 as a reference. Then, if there is any local area determined to have the characteristic "fingerprint" among the local areas of the examined image, the image processing apparatus 10 sets "fingerprint" as the characteristic of this local area. An examination unit 41 of the examination apparatus 40 determines that at least a part of the examined image shows a fingerprint if the characteristic "fingerprint" is set in the received local area characteristic information. Or the characteristic amount vector of an image that should not be determined to have the characteristic "fingerprint" (non-fingerprint image that is difficult to distinguish from a fingerprint) may be stored in the image characteristic database of the image processing apparatus 10. Then, if there is any local area that may be confused with a fingerprint among the local areas of the examined image, the image processing apparatus 10 sets the characteristic of this local area as "non-fingerprint image." The examination unit 41 may determine that the examined image with a local area having "non-fingerprint image" set as its characteristic does not show a fingerprint.

Figure 18:
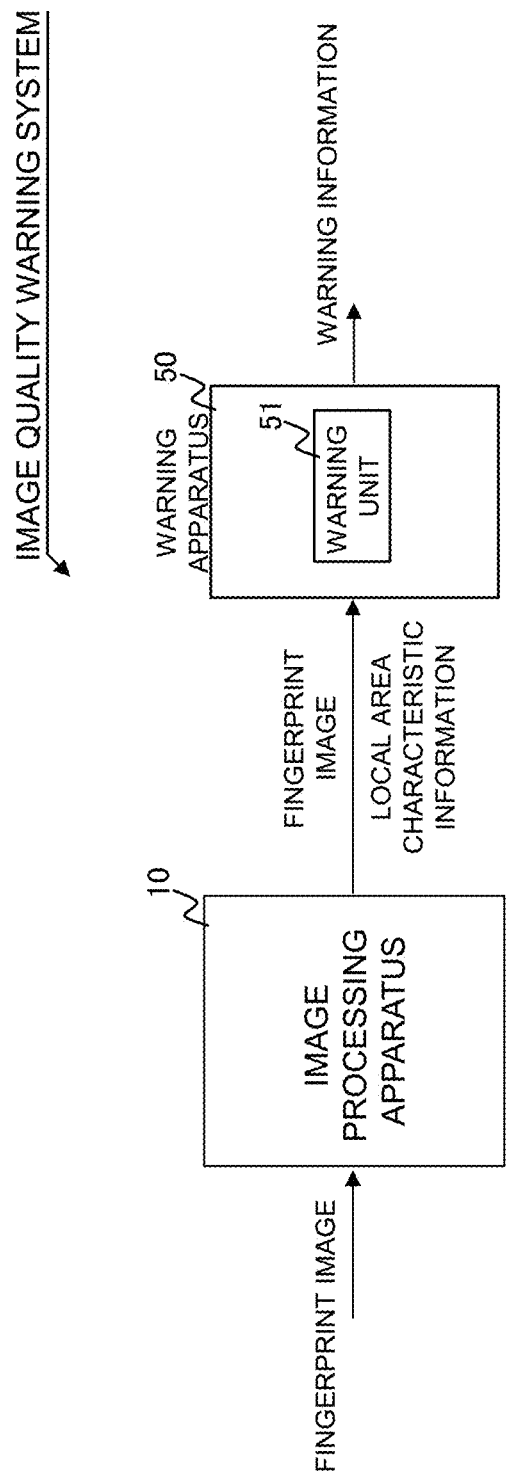
FIG. 18 is a drawing showing an example of an image quality warning system relating to the second exemplary embodiment.

Or as shown in FIG. 18, the image processing apparatus 10 may output the fingerprint image and the local area characteristic information to a warning apparatus 50. When determining that the quality of the fingerprint image is poor, a warning unit 51 of the warning apparatus 50 outputs this information as warning information. In this case, a characteristic amount vector corresponding to a fingerprint image determined to have poor quality is stored in the image characteristic database of the image processing apparatus 10. Then, if there is any local area having a characteristic similar to the one determined to have poor quality among the local areas of the fingerprint image, the image processing apparatus 10 sets the characteristic of this local area as "low quality." The warning unit 51 outputs warning information that the fingerprint image has low quality when there is a local area set as "low quality" in the local area characteristic information.

For instance, the image quality warning system shown in FIG. 18 is suitable for a system that collects fingerprint images using a scanner. The image processing apparatus 10 receives a fingerprint image collected by the scanner and outputs the fingerprint image and the local area characteristic information to the warning apparatus 50. When there is a local area having the characteristic relating to "low quality" in the local area characteristic information, the warning apparatus 50 is able to notify that the quality of the fingerprint image is poor using a lamp and urge the user to reacquire the fingerprint image. Further, the generation of the local area characteristic information by the image processing apparatus 10 can be implemented with a low processing load. This is because the processing relating to the calculation of the LBP characteristic amount and characteristic amount vector can be realized with algorithms of comparing and sorting of numbers. As a result, the local area characteristic information outputted by the image processing apparatus 10 can be suitably utilized for judging the quality of a fingerprint image in real time and for urging the user to reacquire the fingerprint image if necessary.

As described, the local area characteristic information outputted by the image processing apparatus 10 can be used for various purposes without being limited to the selection of the filter applied to the fingerprint image.

[Modification]

Further, any combination of the exemplary embodiments above is included as further exemplary embodiments. For instance, the warning apparatus 50 shown in FIG. 18 may be inserted between the image processing apparatus 10 and the filter apparatus 20 shown in FIG. 2. In this case, the filter apparatus 20 receives only fingerprint images guaranteed by the warning apparatus 50 to have minimum required image quality.

In the first and the second exemplary embodiments, the image processing apparatus 10 receives a fingerprint image as an input image, however, the input image is not limited to fingerprint image. For instance, it may be a palm print image having, just as a fingerprint image, a curved stripe pattern. Or the characteristics of local areas of an image showing the iris pattern of an eye may be identified. In other words, any image having a texture (i.e., visual unevenness) can be a subject of the characteristic determination by the image processing apparatus 10.

In the first exemplary embodiment, the characteristic amount calculation unit 12 calculates the LBP characteristic amount as the image characteristic amount. The image characteristic amount, however, is not limited to the LBP characteristic amount. For instance, a characteristic amount obtained by applying a wavelet transformation to a fingerprint image may be used. More concretely, the characteristic amount calculation unit 12 may use a wavelet coefficient obtained by applying a wavelet transformation to each local area of the fingerprint image as the image characteristic amount characterizing the texture of the local area. In other words, the characteristic amount calculation unit 12 may calculate the image characteristic amount characterizing the texture of a local area by breaking down the pixel values of pixels included in the local area into a plurality of frequency band components. Further, since wavelet transformation is a known technique as described in Japanese Patent Kokai Publication No. JP2004-127064A, the explanation will be omitted.

Or the image characteristic amount calculated by the characteristic amount calculation unit 12 may be a HOG (Histograms of Oriented Gradients) characteristic amount or SIFT (Scale-Invariant Feature Transform) characteristic amount. In other words, as long as it can represent a local texture of an image, any image characteristic amount may be used.

Further, in the first exemplary embodiment, when the characteristic amount calculation unit 12 calculates the LBP value, the distance between the comparison pixel and the center pixel is one pixel, but this may be any number. For instance, the distance between the comparison pixel and the center pixel may be three pixels and five pixels. Further, the LBP value calculated by the characteristic amount calculation unit 12 is not limited to the LBP value calculated by the expression (1) or the LBP value calculated by the technique called rotation-invariant uniform LBP. For instance, the LBP value may calculated using various derivation algorithms.

Further, in the first exemplary embodiment, the characteristic amount vector calculation unit 13 calculates the characteristic amount vector of a local area on the basis of the histogram obtained from the LBP values calculated from the local area with the distance between the comparison pixel and the center pixel being one pixel. The method for calculating the characteristic amount vector, however, is not limited thereto. For instance, the characteristic amount calculation unit 12 calculates the LBP values with the distance between the comparison pixel and the center pixel being three pixels and five pixels. The characteristic amount vector calculation unit 13 may calculate the characteristic amount vector by combining histograms obtained from these LBP values. For instance, the characteristic amount vector calculation unit 13 may use a characteristic amount vector expressed by the following expression (4).

$$FV = \{FV_{C1}, FV_{C3}, FV_{C5}\} \quad (4)$$

Note that $FV_{C1}$ denotes the characteristic amount vector calculated from the histogram when the distance between the comparison pixel and the center pixel is one pixel. $FV_{C3}$ denotes the characteristic amount vector calculated from the histogram when the distance between the comparison pixel and the center pixel is three pixel. $FV_{C5}$ denotes the characteristic amount vector calculated from the histogram when the distance between the comparison pixel and the center pixel is five pixel.

As described, the characteristic amount vector calculation unit 13 may multiplex the characteristic amount vectors calculated from the LBP values having different distances between the comparison pixel and the center pixel. Textures from different viewpoints are quantified by calculating the characteristic amount vector from the LBP values having different distances between the comparison pixel and the center pixel. As a result, the accuracy of identifying the characteristic of a local area by the image processing apparatus 10 improves.

Further, the characteristic amount vectors calculated from images the characteristics of which have been determined are stored in the image characteristic database constructed in the storage unit 16, but the database may store data relating to the images the characteristics of which have been determined. In other words, when the system allows the processing time required for calculating the characteristic amount vector from the image data, the characteristic identification unit 14 may calculate the characteristic amount vector from the images stored in the database as necessary to identify the characteristic.

Further, the characteristic of each image registered in the image characteristic database is not limited to a single characteristic. For instance, some fingerprint images simultaneously show sweat gland pores and faded ridges in the same local area. Even in such a case, as shown in FIG. 19, the image processing apparatus 10 is able to accurately identify these characteristics by registering the characteristic amount vectors calculated from these images having the two characteristics.

Further, the more fingerprint images are used when the image characteristic database is constructed, the better. Even when local areas of fingerprint images have the same characteristic (for instance sweat gland pores or fadedness), their textures may be subtly different. Therefore, by preparing a lot of reference information and registering many characteristic amount vectors in the image characteristic database, the accuracy of identifying a characteristic by the image processing apparatus 10 improves.

When determining the similarity between two characteristic amount vectors (histograms), the characteristic identification unit 14 uses the chi-squared distance as an index. Other indexes such as the Euclidean distance, however, may be used when the similarity between characteristic amount vectors is determined. It should be noted that the chi-squared distance does not strictly compare the similarity between two characteristic amount vectors and allows some differences. Since, it is rare that, for instance, the textures of fingerprint images on the inquiry and registration sides exactly match, the chi-squared distance is suitable as an index for measuring the similarity between two characteristic amount vectors.

The characteristic identification unit 14 may comprise a function (machine learning function) of learning a model by receiving the characteristic of an image whose characteristic has been determined in advance and a characteristic amount vector corresponding to the image whose characteristic has been determined in advance as training data. The characteristic identification unit 14 may identify the characteristic of a local area corresponding to a characteristic amount vector calculated by the characteristic amount vector calculation unit 13 on the basis of the learned model. Further, learning methods using training data include a method using a support vector machine.

Figure 20:
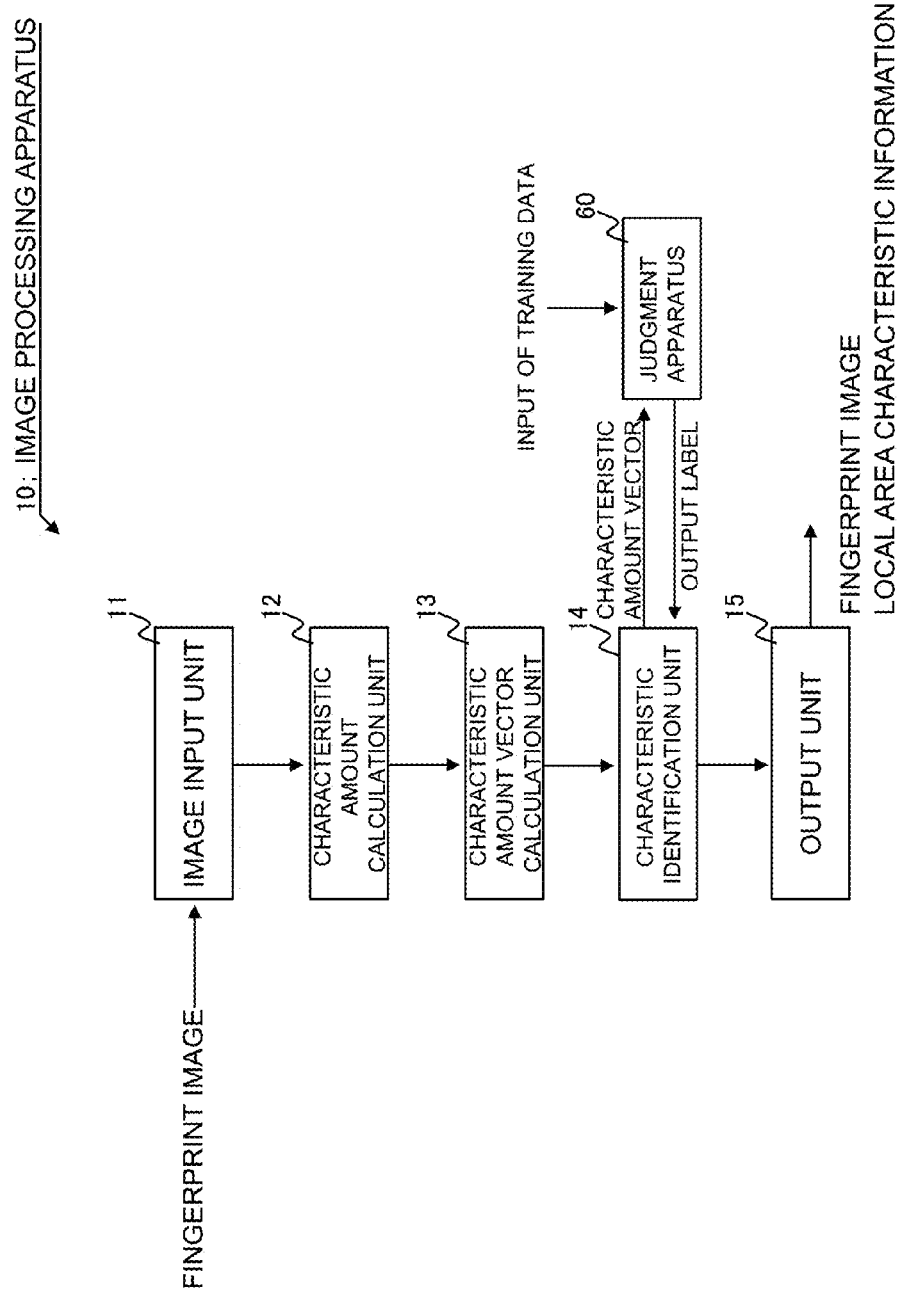
FIG. 20 is a drawing showing another example of the internal configuration of the image processing apparatus.
Figure 21A:
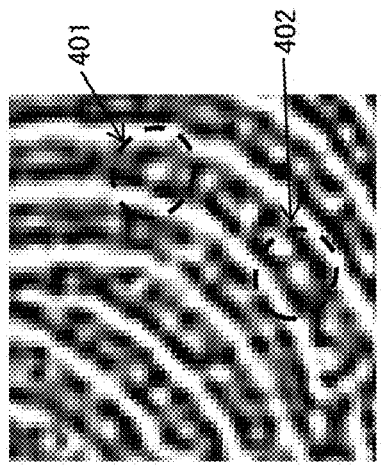
FIG. 21A is an example of a fingerprint image.
Figure 21B:
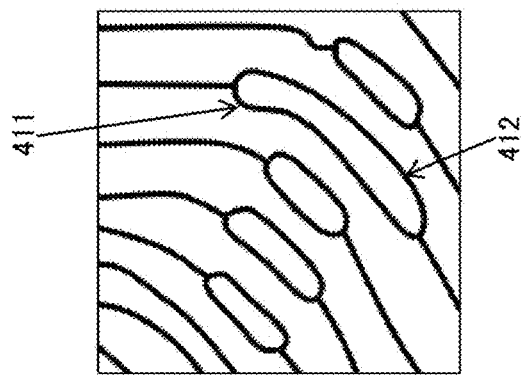
FIGS. 21B and 21C are examples of ridge structures extracted from the fingerprint image.
Figure 21C:
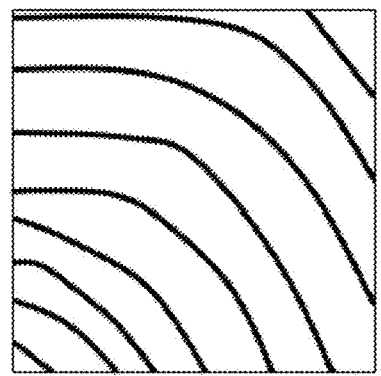

Or the characteristic identification unit 14 may supply the characteristic amount vector to an external judgment apparatus and obtain the characteristic of a local area from the judgment apparatus. For instance, as shown in FIG. 20, a judgment apparatus 60 comprising a machine learning function receives the characteristic of an image whose characteristic has been determined in advance and a characteristic amount vector corresponding to the image whose characteristic has been determined in advance as input of training data. In other words, the characteristic identification unit 14 may entrust an operation of identifying the characteristic of a local area to the external judgment apparatus 60.

The local area characteristic information (refer to FIG. 11) outputted by the output unit 15 may not include the location information and the characteristic thereof regarding all the local areas constituting the fingerprint image. For instance, when it is unnecessary to notify an apparatus following the image processing apparatus 10 of areas that do not show any part of the fingerprint (local areas having the characteristic relating to "no fingerprint"), the output unit 15 may exclude the local areas having the characteristic relating to "no fingerprint" from the local area characteristic information.

In the first exemplary embodiment, the filter apparatus 20 performs the filter processing suitable for each local area. At this time, the filter apparatus 20 may integrate local areas having the same characteristic and apply the filter processing to the fingerprint image corresponding to the integrated local areas collectively. For instance, in FIG. 14B, the filter apparatus 20 may perform the filter processing collectively on areas corresponding to the areas 302 and 303 of the fingerprint image.

Further, the configurations shown in FIGS. 2 and 5 are examples, and the configurations of each system and of the image processing apparatus 10 are not limited thereto. For instance, the image characteristic database constructed in the storage unit 16 may be constructed in a database server installed outside the image processing apparatus 10. Or the main function (the filter unit 22) of the filter apparatus 20 shown in FIG. 2 may be incorporated into the image processing apparatus 10, and the image processing apparatus 10 may perform the filter processing on the input image. Similarly, the main functions (the extraction unit 31, the examination unit 41 and the warning unit 51) of the extraction apparatus 30, the examination apparatus 40, and the warning apparatus 50 shown in FIGS. 16 to 18 may be incorporated into the image processing apparatus 10.

Further, the processing performed by each unit included in the image processing apparatus 10 such as the characteristic amount calculation unit 12 can be realized by a computer program having a computer built into the image processing apparatus 10 execute each processing described above using the hardware thereof. In other words, means for executing the functions performed by the characteristic amount calculation unit 12, etc., using hardware and/or software should be provided.

Further, one can have a computer function as the image processing apparatus by installing the computer program described above on the storage unit of the computer. Furthermore, an image processing method can be performed by the computer by having the computer execute the computer program described above. Further, the program can be updated by download via a network or using a storage medium storing the program.

Some or all of the exemplary embodiments above can be described as the modes below without being limited thereto.

[Mode 1]
An image processing apparatus comprising:
an input unit that receives input of an image;
a characteristic amount calculation unit that calculates an image characteristic amount characterizing a texture of a local area of the input image received by the input unit;
a characteristic amount vector calculation unit that calculates a first characteristic amount vector corresponding to the local area from the image characteristic amount; and
a characteristic identification unit that identifies the characteristic of the local area on the basis of the first characteristic amount vector and a second characteristic amount vector calculated by the same method as the first characteristic amount vector and calculated from an image whose characteristic has been determined in advance, and the first characteristic amount vector.

[Mode 2]
The image processing apparatus of Mode 1, wherein the characteristic amount calculation unit calculates an LBP (Local Binary Pattern) value from each of a plurality of pixels constituting the local area and calculates as the image characteristic amount a histogram of the LBP values that correspond to the plurality of pixels included in the local area, respectively.

[Mode 3]
The image processing apparatus of Mode 2, wherein the characteristic amount vector calculation unit calculates the first characteristic amount vector by selecting a predetermined class from classes constituting the histogram and regarding a frequency belonging to the selected class as an element.

[Mode 4]
The image processing apparatus according to any one of Modes 1 to 3, wherein
the characteristic identification unit calculates a similarity between the first characteristic amount vector and the second characteristic amount vector and identifies the characteristic of the local area on the basis of the similarity.

[Mode 5]

The image processing apparatus of Mode 4 further comprising:

a storage unit that associates a characteristic of the image whose characteristic has been determined in advance with the second characteristic amount vector and stores a result of the association, wherein the characteristic identification unit sets a characteristic corresponding to the second characteristic amount vector having the highest similarity to the first characteristic amount vector among a plurality of the second characteristic amount vectors stored in the storage unit as the characteristic of the local area.

[Mode 6]

The image processing apparatus of Mode 5, wherein the characteristic amount calculation unit calculates a plurality of the local areas by dividing the received image into a plurality of areas, the characteristic identification unit repeats calculating the similarity between the first and the second characteristic amount vectors and identifying the characteristic of each of the plurality of local areas, and calculates local area characteristic information that associates location information of each of the plurality of local areas of the received image with the characteristic of each of the plurality of local areas.

[Mode 7]

The image processing apparatus according to any one of Modes 4 to 6, wherein the characteristic identification unit uses a chi-squared distance as an index for measuring the similarity between the first and the second characteristic amount vectors.

[Mode 8]

The image processing apparatus according to any one of Modes 1 to 7, wherein the received image is an image in which a curved stripe pattern is formed by ridges.

[Mode 9]

The image processing apparatus according to any one of Modes 1 to 3, wherein the characteristic identification unit learns a model by receiving as training data the characteristic of the image whose characteristic has been determined in advance and a second characteristic amount vector corresponding to the image whose characteristic has been determined in advance, and identifies the characteristic of a local area corresponding to the first characteristic amount vector on the basis of the learned model.

[Mode 10]

The image processing apparatus according to any one of Modes 6 to 8 further comprising a filter unit that changes processing applied to each of the plurality of local areas according to the local area characteristic information.

[Mode 11]

The image processing apparatus according to any one of Modes 6 to 8 further comprising at least one of the following:

an extraction unit that extracts the local area having a specific characteristic from the received image on the basis of the local area characteristic information;

an examination unit that examines whether or not a local area having a specific characteristic exists among a plurality of local areas constituting the received image on the basis of the local area characteristic information; and a warning unit that gives a warning regarding quality of the received image on the basis of the local area characteristic information.

[Mode 12]

An image processing method including:

a step of receiving input of an image;

a step of calculating an image characteristic amount characterizing a texture of a local area of the received input image;

a step of calculating a first characteristic amount vector corresponding to the local area from the image characteristic amount; and a step of identifying the characteristic of the local area on the basis of a second characteristic amount vector calculated by the same method as the first characteristic amount vector and calculated from an image whose characteristic has been determined in advance, and the first characteristic amount vector.

[Mode 13]

A program having a computer that controls an image processing apparatus execute:

a process of receiving input of an image;

a process of calculating an image characteristic amount characterizing a texture of a local area of the received input image;

a process of calculating a first characteristic amount vector corresponding to the local area from the image characteristic amount; and a process of identifying the characteristic of the local area on the basis of a second characteristic amount vector calculated by the same method as the first characteristic amount vector and calculated from an image whose characteristic has been determined in advance, and the first characteristic amount vector.

It should be noted that Modes 12 and 13 can be developed into Modes 2 to 11 as Mode 1.

Further, the disclosure of each Patent Literature cited above is incorporated herein in its entirety by reference thereto. It should be noted that other objects, features and aspects of the present invention will become apparent in the entire disclosure and that modifications may be done without departing the gist and scope of the present invention as disclosed herein and claimed as appended herewith. Also it should be noted that any combination of the disclosed and/or claimed elements, matters and/or items may fall under the modifications. Particularly, the ranges of the numerical values used in the present description should be interpreted as a numeric value or small range example included in these ranges even in cases where no explanation is provided.

REFERENCE SIGNS LIST 10, 100: image processing apparatus
11: image input unit
12, 102: characteristic amount calculation unit
13, 103: characteristic amount vector calculation unit
14, 104: characteristic identification unit
15: output unit
16: storage unit
20: filter apparatus
21: input unit
22: filter unit
23: output unit
30: extraction apparatus
31: extraction unit
40: examination apparatus
41: examination unit 50: warning apparatus
51: warning unit
60: judgment apparatus
101: input unit
201 to 203: local block
210: center pixel
211 to 218: comparison pixel
311 to 314, 321: receiver operating characteristic curve
301 to 303, 401, 402: area
411, 412: ridge

What is claimed is:

1. An image processing apparatus, comprising:
an input unit, implemented by hardware, including a processor and a memory storing program code that the processor is to execute, and that receives an image;
a characteristic amount calculation unit implemented at least by the hardware and that calculates an image characteristic amount characterizing a texture of a local area of the image received by the input unit;
a characteristic amount vector calculation unit implemented at least by the hardware and that calculates a first characteristic amount vector corresponding to the local area from the image characteristic amount; and
a characteristic identification unit implemented at least by the hardware and that identifies a characteristic of the local area on the basis of the first characteristic amount vector and a second characteristic amount vector calculated by the same method as the first characteristic amount vector and calculated from an image whose characteristic has been determined in advance, wherein
the characteristic amount calculation unit calculates an LBP (Local Binary Pattern) value from each of a plurality of pixels constituting the local area and calculates as the image characteristic amount a histogram of the LBP values that correspond to the plurality of pixels included in the local area, respectively;
the characteristic amount calculation unit calculates a plurality of the LBP values having different distances between a comparison target pixel and a central pixel; and
the characteristic amount vector calculation unit calculates the first characteristic amount vector by combining histograms obtained from the plurality of LBP values.

2. The image processing apparatus according to claim 1, wherein
the characteristic amount calculation unit calculates an LBP (Local Binary Pattern) value from each of a plurality of pixels constituting the local area and calculates as the image characteristic amount a histogram of the LBP values that correspond to the plurality of pixels included in the local area, respectively.

3. The image processing apparatus according to claim 2, wherein
the characteristic amount vector calculation unit calculates the first characteristic amount vector by selecting a predetermined class from classes constituting the histogram and regarding a frequency belonging to the selected class as an element.

4. The image processing apparatus according to claim 1, wherein
the characteristic identification unit calculates a similarity between the first characteristic amount vector and the second characteristic amount vector and identifies the characteristic of the local area on the basis of the similarity.

5. The image processing apparatus according to claim 4 further comprising:
a storage unit implemented at least by the hardware and that associates a characteristic of the image whose characteristic has been determined in advance with the second characteristic amount vector and stores a result of the association, wherein
the characteristic identification unit sets a characteristic corresponding to the second characteristic amount vector having the highest similarity to the first characteristic amount vector among a plurality of the second characteristic amount vectors stored in the storage unit as the characteristic of the local area.

6. The image processing apparatus according to claim 5, wherein
the characteristic amount calculation unit calculates a plurality of the local areas by dividing the received image into a plurality of areas,
the characteristic identification unit repeats calculating the similarity between the first and the second characteristic amount vectors and identifying the characteristic of each of the plurality of local areas, and calculates local area characteristic information that associates location information of each of the plurality of local areas of the received image with the characteristic of each of the plurality of local areas.

7. The image processing apparatus according to claim 6 further comprising a filter unit implemented at least by the hardware and that changes processing applied to each of the plurality of local areas according to the local area characteristic information.

8. The image processing apparatus according to claim 6 further comprising at least one of the following:
an extraction unit implemented at least by the hardware and that extracts the local area having a specific characteristic from the received image on the basis of the local area characteristic information;
an examination unit implemented at least by the hardware and that examines whether or not a local area having a specific characteristic exists among a plurality of local areas constituting the received image on the basis of the local area characteristic information; and
a warning unit implemented at least by the hardware and that gives a warning regarding quality of the received image on the basis of the local area characteristic information.

9. The image processing apparatus according to claim 4, wherein
the characteristic identification unit uses a chi-squared distance as an index for measuring the similarity between the first and the second characteristic amount vectors.

10. The image processing apparatus according to claim 1, wherein the received image is an image in which a curved stripe pattern is formed by ridges.

11. The image processing apparatus according to claim 1, wherein
the characteristic identification unit learns a model by receiving as training data the characteristic of the image whose characteristic has been determined in advance and a second characteristic amount vector corresponding to the image whose characteristic has been determined in advance, and identifies the characteristic of a local area corresponding to the first characteristic amount vector on the basis of the learned model.

12. An image processing method, comprising:
receiving an image;
calculating an image characteristic amount characterizing a texture of a local area of the received image;
calculating a first characteristic amount vector corresponding to the local area from the image characteristic amount; and
identifying a characteristic of the local area on the basis of the first characteristic amount vector and a second characteristic amount vector calculated by the same method as the first characteristic amount vector and calculated from an image whose characteristic has been determined in advance, wherein
calculating the image characteristic amount comprises calculating an LBP (Local Binary Pattern) value from each of a plurality of pixels constituting the local area and calculates as the image characteristic amount a histogram of the LBP values that correspond to the plurality of pixels included in the local area, respectively;
calculating the image characteristic amount comprises calculating a plurality of the LBP values having different distances between a comparison target pixel and a central pixel; and
calculating the first characteristic amount vector comprises calculating the first characteristic amount vector by combining histograms obtained from the plurality of LBP values.

13. A non-transitory computer-readable recording medium storing a program having a computer that controls an image processing apparatus execute:
a process of receiving an image;
a process of calculating an image characteristic amount characterizing a texture of a local area of the received image;
a process of calculating a first characteristic amount vector corresponding to the local area from the image characteristic amount; and
a process of identifying a characteristic of the local area on the basis of the first characteristic amount vector and a second characteristic amount vector calculated by the same method as the first characteristic amount vector and calculated from an image whose characteristic has been determined in advance, wherein
the process of calculating the image characteristic amount calculates an LBP (Local Binary Pattern) value from each of a plurality of pixels constituting the local area and calculates as the image characteristic amount a histogram of the LBP values that correspond to the plurality of pixels included in the local area, respectively;
the process of calculating the image characteristic amount calculates a plurality of the LBP values having different distances between a comparison target pixel and a central pixel; and
the process of calculating the first characteristic amount vector calculates the first characteristic amount vector comprises calculating the first characteristic amount vector by combining histograms obtained from the plurality of LBP values.

* * * * *